US012733876B2

(12) United States Patent
Andersen et al.

(10) Patent No.: US 12,733,876 B2
(45) Date of Patent: Sep. 15, 2026

(54) EFFICIENTLY STORING DATA FOR WIDE DYNAMIC RANGE AND HIGH RESOLUTION BIOLOGICAL SIGNALS

(71) Applicant: Pacesetter, Inc., Sylmar, CA (US)

(72) Inventors: Dean Andersen, San Jose, CA (US); Xing Pei, Thousand Oaks, CA (US); David Doudna, Sunnyvale, CA (US); Reza Shahandeh, Tarzana, CA (US)

(73) Assignee: Pacesetter, Inc., Sylmar, CA (US)

( * ) Notice: Subject to any disclaimer, the term of this patent is extended or adjusted under 35 U.S.C. 154(b) by 1078 days.

(21) Appl. No.: 17/858,839

(22) Filed: Jul. 6, 2022

(65) Prior Publication Data

US 2023/0067795 A1 Mar. 2, 2023

Related U.S. Application Data

(60) Provisional application No. 63/237,339, filed on Aug. 26, 2021.

(51) Int. Cl.
*A61N 1/375* (2006.01)
*A61B 5/00* (2006.01)

(52) U.S. Cl.
CPC ............ *A61B 5/686* (2013.01); *A61N 1/3756* (2013.01); *A61N 1/37512* (2017.08)

(58) Field of Classification Search
CPC ... A61B 5/686; A61N 1/3756; A61N 1/37512
USPC ........................................................... 607/36
See application file for complete search history.

(56) References Cited

U.S. PATENT DOCUMENTS

| | | | |
|---|---|---|---|
| 5,047,768 A | 9/1991 | Yamaguchi et al. | |
| 5,215,098 A | 6/1993 | Steinhaus et al. | |
| 5,819,740 A | 10/1998 | Muhlenberg | |
| 6,599,242 B1 | 7/2003 | Splett et al. | |
| 7,142,924 B2 | 11/2006 | Legay et al. | |
| 7,634,310 B2 | 12/2009 | Lee et al. | |
| 8,064,992 B2 | 11/2011 | Henry et al. | |
| 8,200,322 B2 | 6/2012 | Ousdigian et al. | |
| 10,617,320 B2 | 4/2020 | Mahajan et al. | |
| 10,624,551 B2 | 4/2020 | Bardy et al. | |
| 10,702,167 B2 | 7/2020 | Mahajan et al. | |
| 2020/0129082 A1* | 4/2020 | Andersen | A61B 5/364 |

FOREIGN PATENT DOCUMENTS

| | | |
|---|---|---|
| EP | 1537894 B1 | 3/2007 |
| EP | 1477906 B1 | 10/2018 |

* cited by examiner

*Primary Examiner* — Benjamin J Klein
(74) *Attorney, Agent, or Firm* — Pearl Cohen LLP

(57) ABSTRACT

Described herein are methods, devices and systems for efficiently storing data for sensed biological signals. A sensed biological signal, or an amplitude and/or filtered version thereof, is provided to an N-bit ADC of an IMD to produce an N-bit data value indicative of an amplitude of the biological signal at a point in time. One of a plurality of chords of a compression curve is selected, based on a magnitude of the N-bit data value, and used to produce an M-bit data value, which is a compressed version of the N-bit data value, wherein M<N. The M-bit data value is stored as an M-bit data slice within memory of the IMD, and can be expanded to a reproduced N-bit data value after being uploaded to a non-implanted device or system.

19 Claims, 16 Drawing Sheets

912

| Input Code | Output Code |
|---|---|
| 0-100 | 0 |
| 101-200 | 8 |
| 101-400 | 16 |
| 401-800 | 24 |

EFFICIENTLY STORING DATA FOR WIDE DYNAMIC RANGE AND HIGH RESOLUTION BIOLOGICAL SIGNALS

PRIORITY CLAIMS

This application claims priority to U.S. Provisional Patent Application No. 63/237,339, filed Aug. 26, 2021, which is incorporated herein by reference in its entirety.

FIELD

Embodiments described herein relate to methods, devices, and systems that efficiently store wide dynamic range and high resolution biological signals, such as electrocardiogram (ECG) or electrogram (EGM) signals, and more specifically, data indicative thereof, in memory of an implantable medical device (IMD).

BACKGROUND

An IMD often includes electrodes that enable the IMD to sense an ECG signal or an EGM signal, which can be referred to collectively as an ECG/EGM, or more generally as a signal indicative of cardiac electrical activity. An IMD can alternatively, or additionally, include other types of sensors, besides electrodes, that are used to sense other types of biological signals besides signals indicative of cardiac electrical activity. For example, an IMD can include a pressure sensor that is used to sense a signal indicative of pressure within a cardiac chamber, within a body lumen, and/or the like. For another example, an IMD may include a microphone that is used to sense audio signals, such as, but not limited to, heart sound signals. For still another example, an IMD can include an activity or motion sensor (e.g., an accelerometer) that is used to sense a signal from which patient motion and/or posture, or cardiac motion, can be monitored. For still other examples, an IMD can include an optical sensor that can detect a photoplethysmography (PPG) signal, or an impedance sensor that can detect an impedance plethysmography (IPG) signal. Regardless of the type of sensed biological signal, it is often desirable for an IMD to store biological data indicative of the sensed biological signal, which enables the biological signal to be reproduced and observed (and/or otherwise analyzed) after being uploaded to a non-implanted device and/or system.

Due to the limited memory, processing, and power resources of an IMD, it is often desirable to store relatively low-bit sampled data (e.g., 8-bit sampled data) for an ECG/EGM or other type of biological signal. However, having only 8-bit sampled data for an ECG/EGM or other biological signal can be limiting due to 8-bits only being able to accurately reproduce a dynamic range of 256 counts. For example, with a full-scale range of +/−1 mV, the minimum resolution that can be displayed is 8 microvolts (μV). Depending on the electrodes and/or lead combination, the amplitude of a typical P-wave may only be 25-50 μV. This may only represent 3 to 6 counts of resolution, should an 8-bit analog-to-digital converter (ADC) be used to convert the ECG/EGM from an analog signal to a digital signal. At the low end of this range, this may be unacceptable to identify a P-wave or a T-wave of an ECG/EGM, or to identify certain features of other types of biological signals.

Where a biological signal being sampled by an ADC of a sensing front end is an ECG/EGM, the gain of the sensing front end may be increased to increase the amplitude of a P-wave, but that may also increase the amplitude of an R-wave to the point of clipping or saturating, which is undesirable.

It would be beneficial if an IMD could efficiently store digital data in a manner that enables an ECG/EGM, and/or other type of biological signal, to be reproduced and viewed with a wide dynamic range and high resolution, so that the morphology of the signal (e.g., after data for the signal has been uploaded from an IMD to a non-implanted device or system, and the signal has been reproduced) can be revealed to provide further clinically relevant information for further processing.

SUMMARY

Certain embodiments of the present technology relate to methods, devices and system that efficiently store data for sensed biological signals. In accordance with certain embodiments, a method, which is for use by an IMD, includes providing the sensed biological signal, or an amplitude and/or filtered version thereof, to an N-bit analog-to-digital converter (ADC) of the IMD, wherein N>8. Additionally, the method includes outputting, from the N-bit ADC of the IMD, an N-bit data value indicative of an amplitude of the biological signal at a point in time. The method further includes, selecting one of a plurality of chords of a compression curve based on which one of a plurality magnitude ranges a magnitude of the N-bit data value output from the ADC is within, and using the selected one of the plurality of chords of the compression curve to produce an M-bit data value, which is a compressed version of the N-bit data value output from the ADC, wherein M<N. Additionally, the method includes storing the M-bit data value, or a filtered and/or amplified version thereof, as an M-bit data slice within memory of the IMD, so that the M-bit data value, or a filtered and/or amplified version thereof, can be expanded to a reproduced N-bit data value after being uploaded to a non-implanted device or system. The method also includes repeating the outputting, selecting, using, and storing steps for a plurality of additional N-bit data values indicative of amplitudes of the biological signal at a plurality of additional points in time, so that a plurality of M-bit data values, or filtered and/or amplified versions thereof, are stored as a plurality of M-bit data slices within the memory of the IMD. In accordance with certain embodiments, 16>N>8, and M=8.

The method can additionally include, sensing the biological signal using a sensor or electrodes of, or communicatively coupled to, the IMD. The biological signal can be, e.g., an EGM or ECG indicative of cardiac electrical activity, a plethysmography signal indicative of cardiac mechanical activity, a signal indicative of heart sounds, a signal indicative of body temperature, a signal indicative of motion, a signal indicative of blood pressure, or a cardiogenic impedance signal, but is not limited thereto. The IMD can be, e.g., a pacemaker coupled to one or more transvenous leads, a leadless pacemaker, an insertable cardiac monitor (ICM), or an implantable cardioverter defibrillator (ICD), but is not limited thereto. Further examples of sensed biological signals include a signal indicative of pressure within a cardiac chamber, and a signal indicative of pressure within a body lumen, such as an artery or vein.

In accordance with certain embodiments, the plurality of M-bit data values, or filtered and/or amplified versions thereof, that are stored in the memory of the IMD are uploaded to a non-implanted device or system so that the M-bit data values, or filtered and/or amplified versions thereof, can be expanded to a provide a plurality of N-bit reproduced data values, by the non-implanted device or system, and so that the N-bit reproduced values can be used by the non-implanted device or system to generate a reproduced version of the biological signal.

The method can also include storing a plurality of look up tables (LUTs) in registers or memory of the IMD, wherein each of the LUTs corresponds to a respective one of the plurality of chords of the compression curve. In such embodiments, the selecting one of the plurality of chords of the compression curve comprises selecting one of the plurality of LUTs based on which one of the plurality magnitude ranges the magnitude of the N-bit data value output from the ADC is within, and the using the selected one of the plurality of chords of the compression curve to produce the M-bit data value comprises using the selected one of the plurality of LUTs to produce the M-bit data value.

In accordance with certain embodiments, each LUT, of the plurality of LUTs, has a respective different output value for each of a plurality of different sub-ranges of magnitudes, such that the LUT is used to produce a same one of a plurality of different output values for a plurality of different input values that are within a same one of the sub-ranges of magnitudes.

In accordance with certain embodiments, the method also includes updating one or more of the LUTs stored in the registers or memory to thereby modify how the N-bit data values that are output by the ADC are compressed to M-bit data values that are stored in the memory. Such updating can be performed, e.g., in response to instructions from a non-implanted device or system, such as an external programmer.

In accordance with certain embodiments, the selecting (of one of the plurality of chords of the compression curve, or more specifically, of one of the plurality of LUTs) is performed using a plurality of magnitude comparators and a decoder that receives outputs of the magnitude comparators. In certain such embodiments, at any given time, each of the magnitude comparators compares a magnitude of a same one of the N-bit data values to a different one of a plurality of reference values that correspond to boundaries of a plurality of magnitude ranges. The decoder receives the outputs of the magnitude comparators and selects one of the plurality of chords (or more specifically, LUTs) by decoding the outputs of the magnitude comparators.

An IMD, according to an embodiment of the present technology, includes an N-bit ADC, and a compressor. The N-bit ADC is configured to receive a sensed biological signal, or an amplitude and/or filtered version thereof, and output N-bit data values indicative of an amplitude of the biological signal at each of a plurality of points in time, wherein N>8. The compressor is configured to compress the N-bit data values to respective M-bit data values, wherein M<N, so that data for the biological signal can be stored as M-bit data slices within memory of the IMD.

In accordance with certain embodiments, for each of the N-bit data values, the compressor is configured to: select one of a plurality of chords of a compression curve based on which one of a plurality magnitude ranges a magnitude of the N-bit data value output from the ADC is within; use the selected one of the plurality of LUTs to produce an M-bit data value, which is a compressed version of the N-bit data value output from the ADC, wherein M<N; and store the M-bit data value, or a filtered and/or amplified version thereof, as an M-bit data slice within memory of the IMD, so that the M-bit data value can be expanded to a reproduced N-bit data value after being uploaded to a non-implanted device or system.

In accordance with certain embodiments, the IMD also includes at least one of a digital filter and a digital amplifier, between the N-bit ADC and the compressor, configured to filter and/or amplify the N-bit data values output from the ADC before the N-bit data values are provided to the compressor.

In accordance with certain embodiments, the compressor comprises a plurality of magnitude comparators and a decoder that receives outputs of the magnitude comparators. At any given time, each of the magnitude comparators compares a magnitude of a same one of the N-bit data values to a different one of a plurality of reference values that correspond to boundaries of the plurality of magnitude ranges. The decoder receives the outputs of the magnitude comparators and selects one of the plurality of chords of the compression curve by decoding the outputs of the magnitude comparators.

In accordance with certain embodiments, the IMD includes memory or registers that store a plurality of look up tables (LUTs), wherein each of the LUTs corresponds to a respective one of the plurality of chords of the compression curve. In certain such embodiments, the compressor is configured to select one of the plurality of chords of the compression curve by selecting one of the plurality of LUTs based on which one of the plurality magnitude ranges the magnitude of the N-bit data value output from the ADC is within, and the compressor is configured to use the selected one of the plurality of chords of the compression curve to produce the M-bit data value by using the selected one of the plurality of LUTs to produce the M-bit data value.

In accordance with certain embodiments, each LUT, of the plurality of LUTs, has a respective different output value for each of a plurality of different sub-ranges of magnitudes, such that the LUT is used to produce a same one of a plurality of different output values for a plurality of different input values that are within a same one of the sub-ranges of magnitudes.

In accordance with certain embodiments, in response to receiving instructions from a non-implantable device, the compressor is configured to update one or more of the LUTs stored in the registers or memory to thereby modify how N-bit data values that are output by the ADC are compressed to M-bit data values that are stored in the memory.

A method for efficiently storing data for a sensed biological signal in memory of an IMD, comprises storing a plurality of LUTs, each of which corresponds to a respective one of a plurality of chords associated with a compression curve, and converting an analog signal, which corresponds to a sensed biological signal, to a digital signal that comprises a plurality of N-bit data values, wherein N>8. The method also comprises for each N-bit data value, of the plurality of N-bit data values, compressing the N-bit data value to an M-bit data value and storing the M-bit data value in the memory of the IMD, so that a plurality of M-bit data values can be uploaded to a non-implanted device or system that can produce a reconstructed version of the sensed biological signal based on the plurality of M-bit data values, wherein M<N. In accordance with certain embodiments, the compressing comprises, for each N-bit data value, of the plurality of N-bit data values, selecting one of the plurality of LUTs based on a value of the N-bit data value, and using the selected one of the plurality of LUTs to produce the M-bit data value, which is a compressed version of the N-bit data value. In accordance with certain embodiments, the selecting one of the plurality of LUTs, which is part of the compressing an N-bit data value to an M-bit data value, is based on which one of a plurality magnitude ranges a magnitude of the N-bit data value that is being compressed is within. The method can also include updating one or more of the LUTs to thereby modify how further N-bit data values are compressed to further M-bit data values that are stored in the memory.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology, described herein, enable a high resolution ECG/EGM signal (or other type of biological signal) to be stored with an 8-bit system for efficiency, and later be reproduced to substantially its original high resolution and wide dynamic range signal. Such embodiments beneficially allow wide dynamic range signals, like ECG/EGM signals, to be displayed without compromising either the relatively small amplitude signal features, such as P-waves and/or T-waves, or the large amplitude signal features, such as R-waves.

Preferably, the recording and storing of biological signal data in an IMD are performed in power efficient manners to ensure long IMD longevity. For a typical cardiac device, biological signal data is stored constantly, or at least often. Therefore, to conserve power, it is desirable to store biological signal data in a least number of bits and bytes as practical to conserve power.

Predominately, most microprocessor data paths of an IMD are in integer multiples of 8-bits wide. While older processors had data paths that were 8-bits wide, the data paths of newer generation processors became either 16-bits, 32-bits or even a higher number of bits wide. The data paths for data storage is also typically in widths of 8, 16 or 32 bits, most often matching the inherent microprocessor data width. That is to say, even though an IMD may have a 32-bit wide microprocessor and memory, generally 8-bit wide data can still be stored in memory to save power. For an example, four 8-bit data slices can be stored in one 32-bit slot in memory.

Figure 1:
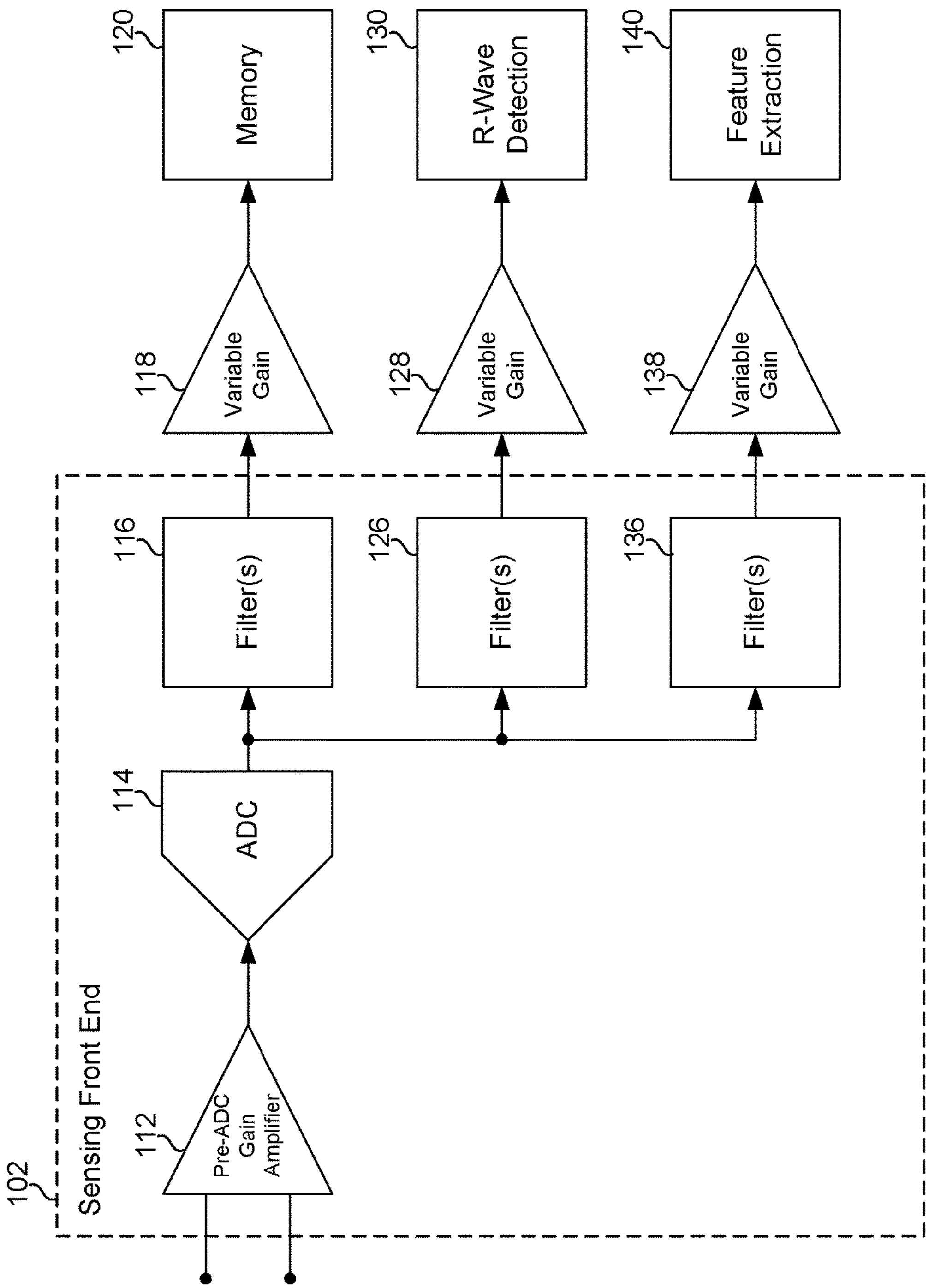
FIG. 1 is a high level block diagram of an example sensing front end of an IMD, and certain circuitry downstream of the sensing front end.

The sensing front end on many integrated circuits (ICs) have a high-resolution analog-to-digital converter (ADC), such as a 14-bit ADC. FIG. 1 is a high level block diagram of an example sensing front end 102 of an IMD, which can also be referred to as a sampling front end 102, or more succinctly as a front end 102. Referring to FIG. 1, the sensing front end 102 is shown as including an analog amplifier 112, an ADC 114, filters 116, 126, 136, digital amplifiers 118, 128, 138, memory 120, an R-wave detection circuit 130, and a feature extraction circuit 140. The analog amplifier 112, which can be a fixed gain pre-ADC amplifier, preferably provides enough gain to the analog biological signal that is to be converted by the ADC 114, so that the ADC 114 can operate properly, wherein the ADC 114 can be a high resolution (e.g., 14-bit) ADC, as noted above, but is not limited thereto. For example, if a sensed biological signal is in the millivolt (mV) range, and the ADC 114 has a reference voltage of 1 volt (V), then the analog amplifier 112 may provide a gain of about 1000 V/V, to enable the ADC 114 to operate properly. For the purpose of this discussion, it is often assumed that the biological signal that is provided to the amplifier 112, and amplified by the amplifier 112, is an ECG/EGM signal. Nevertheless, it should be noted that the signal can alternatively be another type of biological signal, some examples of which are provided herein.

The amplified analog signal, which is output by the analog amplifier 112, is converted to a digital signal by the ADC 114. The digital signal is separately filtered, in parallel, by the filters 116, 126, 136, and then separately amplified, in parallel, but the digital amplifiers 118, 128, and 138 for various processing and memory storage. More specifically, a first digital data path includes one or more filter(s) 116, the digital amplifier 118, and memory 120. A second digital data path includes one or more filter(s) 126, the digital amplifier 128, and the R-wave detection circuit 130. A third digital data path includes one or more filter(s) 136, the digital amplifier 138, and the feature extraction circuit 140. The feature extraction circuit 140 can detect various features of a biological signal, such as, but not limited to, intrinsic responses (e.g., R-waves), evoked responses (e.g., V-waves) to pacing pulses, areas under a portion of a curve, integrations, morphological features, and/or the like. The digital amplifiers 118, 128, and 138 enable a separate gain adjustment for each of the digital data paths. The digital data paths described above can also be referred to as digital signal paths.

For much of the following discussion, it is assumed that the resolution of the ADC 114 is 14-bits, which provides for high resolution. The high resolution provided by the ADC 114 allows for wide dynamic ranges that are beneficial for ECG/EGM recording, as well as the recording of other types of biological signals. An ADC that has 14-bits of resolution can also be referred to as a 14-bit ADC. More generally, an ADC that has N-bits or resolution can be referred to as an N-bit ADC.

Figure 2A:
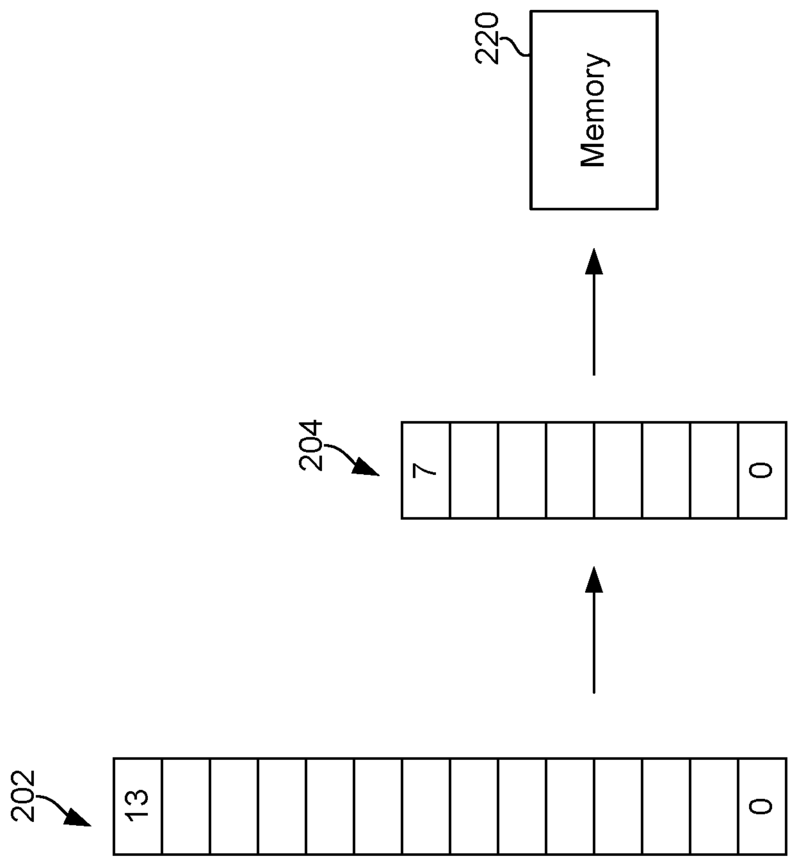
FIG. 2A is a high level illustration of how truncation of digital data, by discarding some uppermost and/or lowermost bits, can be performed to compress an N-bit data value to an M-bit data value that is stored in memory.
Figure 2B:
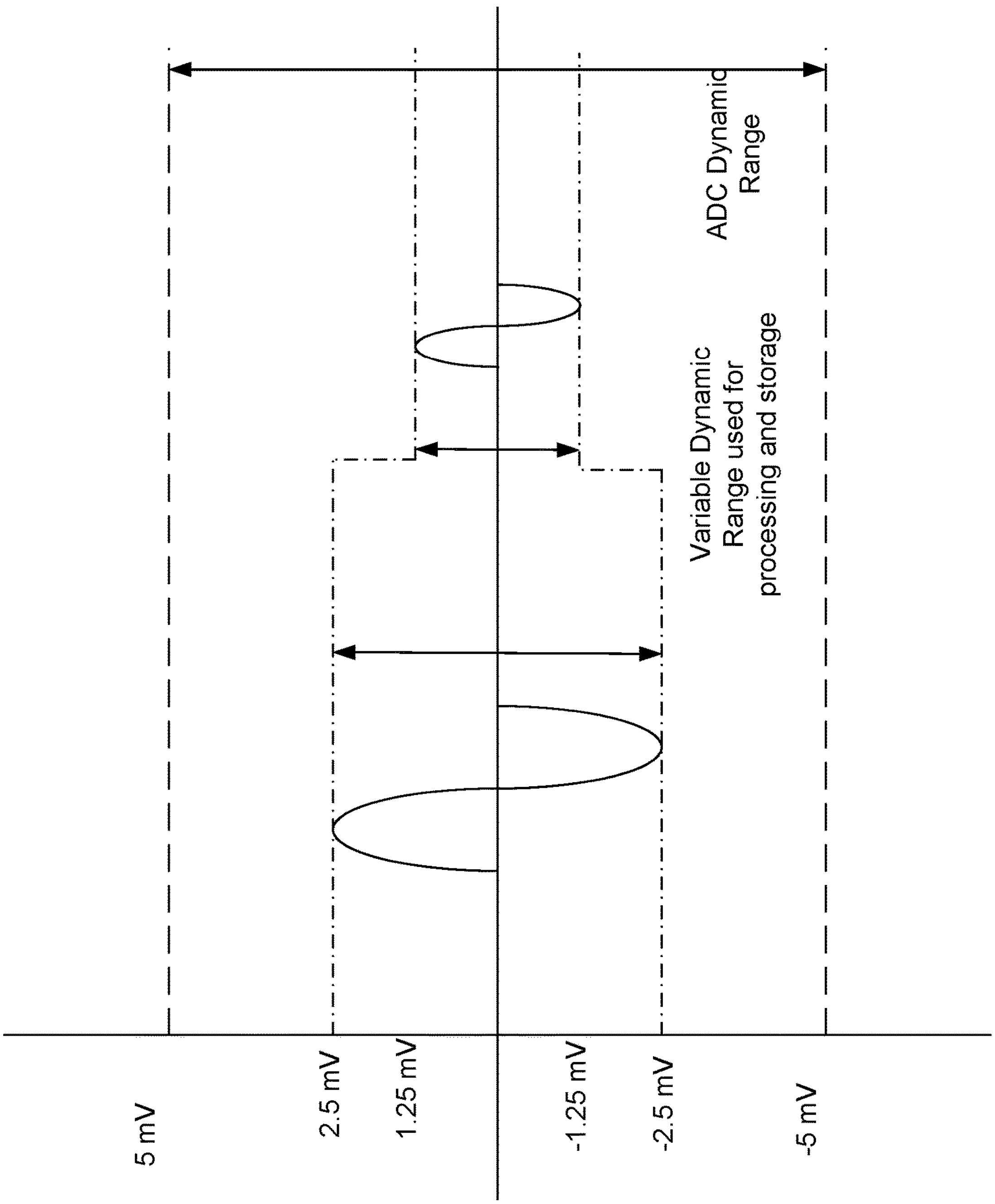
FIG. 2B is a high level illustration of how an N-bit data value can be shifted first (in this example discarding one or two of the upper bits thus reducing dynamic range by a factor of two or four) to scale the M-bit data value to an N-bit data value.

To preserve power and increase storage efficiency, the 14-bits of data that are output by a 14-bit ADC can be truncated to 8-bits. Truncation is performing by choosing an 8-bit segment from a 14-bit data value, or more generally, by choosing of an M-bit segment from an N-bit data value, where N>M (e.g., N=14 and M=8). Referring to FIG. 2A, in one example of truncation, a value represented by 14-bits (labeled 202) can be truncated to a value represented by 8-bits (labeled 204) by selecting the 8 least significant bits (LSBs) and storing the 8 LSBs in a memory 220 (e.g., which can be the memory 120 in FIG. 1). Alternatively, the 14-bit data value can be shifted first, thus scaling the 14-bit data value to an 8-bit data value. An illustration of this operation is shown in FIG. 2B. In other words, 14-bits can be truncated to 8-bits by selecting bits 0 through 7 (i.e., the eight LSBs), or some segment of bits, such as bits 1 through 8, bits 2 through 9, bits 3 through 10, bits 4 through 11, bits 5 through 12, or bits 6 through 13, the latter of which are the eight most-significant bits (MSBs). Use of truncation to create an 8-bit data value from a wider 14-bit data value, or more generally an M-bit data value from a wider N-bit data value, may be acceptable for some purposes. However, the use of truncation to create an 8-bit data value from a wider 14-bit data value, or more generally an M-bit data value from a wider N-bit data value, may be unacceptable for other purposes, especially for signals that have large peak variations.

A goal of certain embodiments of the present technology described herein is to substantially preserve and store a wide dynamic range M-bit signal (e.g., an 8-bit signal) from a wider N-bit signal (e.g., a 14-bit signal), without sacrificing memory storage. Explained another way, a goal of certain embodiments of the present technology described herein is to substantially preserve and store a wider dynamic range N-bit signal (e.g., a 14-bit signal) in narrower M-bit data slices (e.g., 8-bit data slices) without the sacrificing memory storage.

Figure 2C:
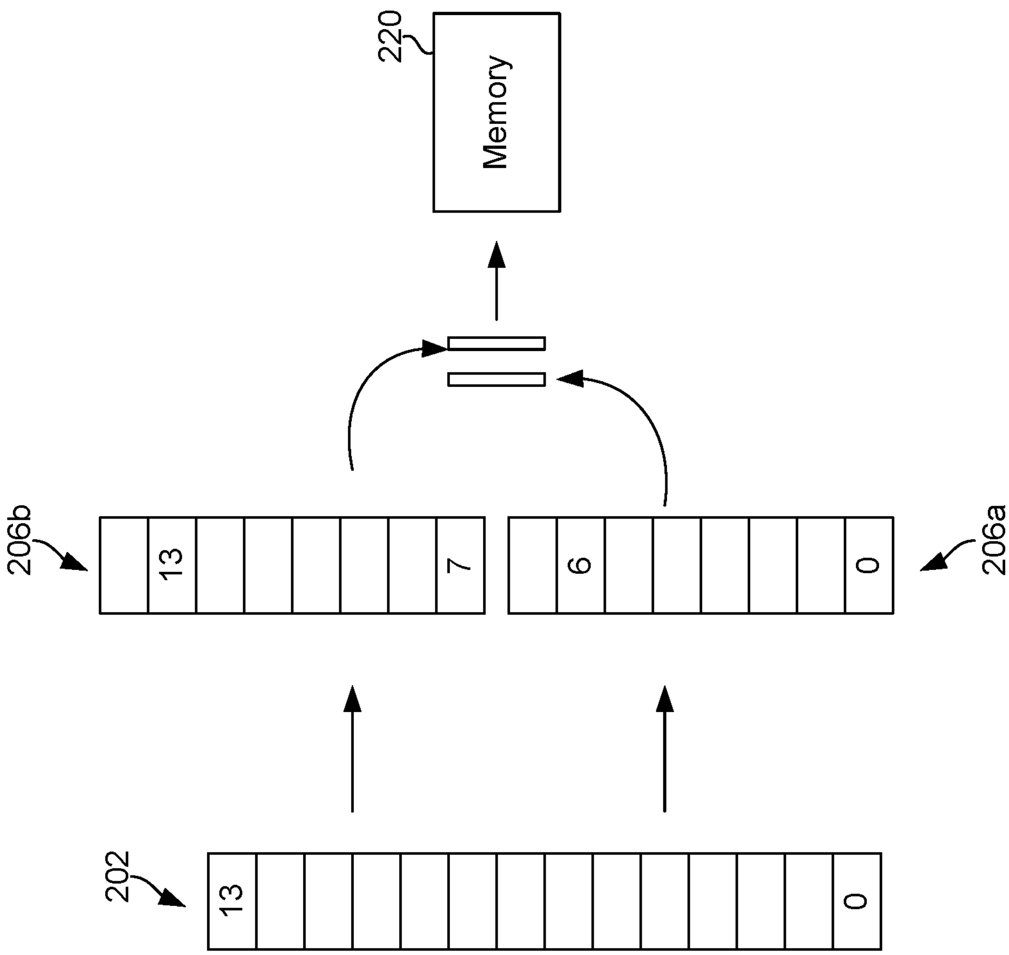
FIG. 2C is a high level illustration of how an N-bit data value can be separated into two data segments that are each N/2-bits, which are sent to memory in a time multiplexed fashion.

One approach is to separate each 14-bit data value (aka 14-bits of data) into two data segments that are each 7-bits, which are sent to memory in a time multiplexed fashion. This approach is illustrated in FIG. 2C, which shows a value represented by 14-bits (labeled 202) being separated into two data segments 206*a*, 206*b*, which are sent to the memory 220 in a time multiplexed fashion, e.g., using a multiplexer (not shown). This approach does not require any computation to format the data, but has the disadvantage of requiring twice as much storage space in the memory 220, compared to if only 8-bits of data were stored for the 14-bit data value (labeled 202).

Certain embodiments of the present technology described herein advantageously use only 8-bits to store a 14-bit data value, or more generally, use only M-bits to store an N-bit data value, where M<N, wherein the 8-bit (and more generally the M-bits) enable the 14-bit data value (and more generally, the N-bit data value) to be substantially reproduced such that a difference between original values and respective reproduce values are within an acceptable amount of error, e.g., within a root mean square (RMS) error of 5%, but not limited thereto.

There are known "companding" techniques (sometimes referred to as "compansion" techniques) for compressing wide bandwidth data to narrower bandwidth data, and then expanding the data later to substantially reproduce the original data. Where the companding is performed using software and/or firmware, algorithms can be used to perform the data compression, which algorithms may involve logarithms and division, causing the computational complexity to potentially be relatively high.

Figure 3:
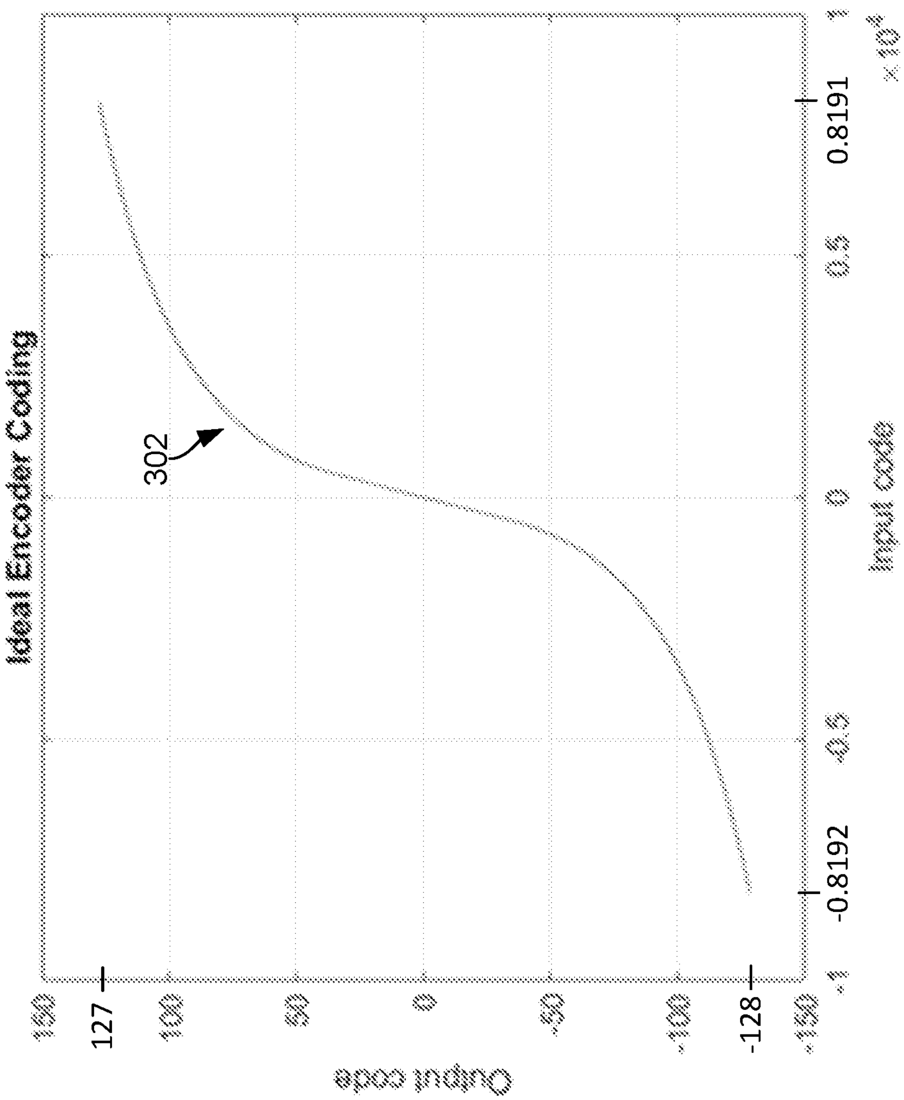
FIG. 3 illustrates an example companding curve that can be used to compress an N-bit data value to an M-bit data value.

Certain embodiments of the present technology disclosed herein utilize a simplification to implement a substantially ideal translation curve. An example compressor transfer function, which is an example of an ideal translation curve 302, and can also be referred to as a companding curve 302, is shown in FIG. 3. The slope of the curve 302 indicates the trade-off between precision and compression for changes in a signal at any input magnitude. In the example companding curve 302 shown in FIG. 3, signal levels near the zero baseline maintain the highest precision, with the lowest compression, transitioning logarithmically to the highest compression as it approaches the maximum magnitude which can be represented by the stored encoding. Note the non-linear nature of the transformation. This was performed using a known transformation called A-law compression.

In FIG. 3, the input code is a 14-bit code, which can be referred to more generally as an ADC count value, or an ADC output value. Since a 14-bit code can represent 16,384 different values, where both negative and positive values are to be represented, the 14-bit input code can represent any value between −8192 and +8191. In FIG. 3, the output code is an 8-bit code, which can be referred to as an encoded value, a companded value, or a compressed value. Since an 8-bit code can represent 256 different values, where both negative and positive values are to be represented, the 8-bit output code can represent any value between −128 and +127. Such negative and positive values can be represented in binary form, for example, using two's complement.

Figure 4A:
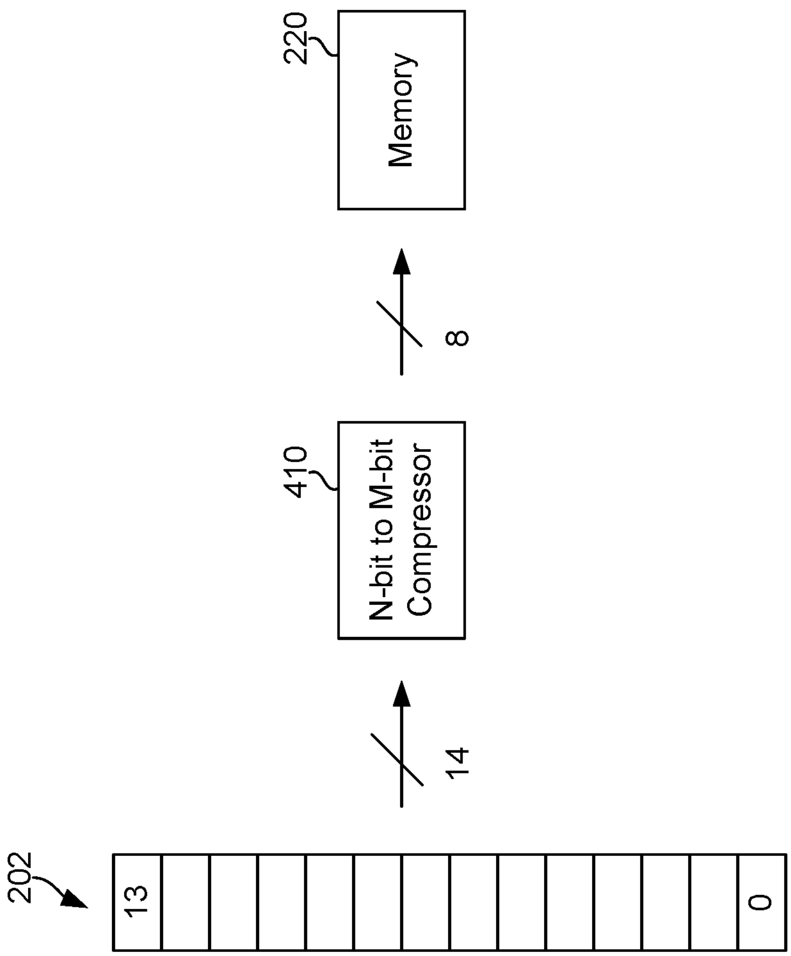
FIG. 4A is a high level illustration of how a compressor can be used to compress an N-bit data value to an M-bit data value that is stored in memory.

FIG. 4A is a high level illustration of how a compressor can be used to compress a 14-bit data value to an 8-bit data value, or more generally an N-bit data value to an M-bit data value, that is stored in memory. As shown in FIG. 4A, in accordance with certain embodiments, the 14-bit data value (labeled 202) is compressed using a compressor 410 and stored in memory 220 as 8-bits. The compressor 410 can be implemented in either hardware or software, or a combination thereof, but preferably would be implemented in hardware in an IMD to reduce power consumption. Also note that the A-law and p-law compression functions that may be implemented by the compressor 410 can be compression functions that have conventionally been used for telephony, as these compression functions have been specifically designed for speech audio signals, not for biological signals. Therefore, these functions may be sub-optimal for compressing ECG/EGM data and other types of biological signal data. It is noted that these embodiments do not require the use of any particular compression function, and for that matter, any particular compressor 410. Rather, almost any arbitrary compression function may be used. In particular, there are many better functions implementing companding curves that are better suited for biological signal applications.

The 8-bit data (or more generally M-bit data) that is produced by companding the 14-bit data value (or more generally, the N-bit data value), and then stored it in the memory 220, can be referred to as companded or compressed 8-bit data (or more generally, a companded or compressed M-bit data). When needed, the companded M-bit data can be uploaded from the IMD to a non-implanted programmer, bedside monitor, or the like. The programmer or other non-implanted device or system then reverses the compression using an expansion transformation, an example of which is shown in FIG. 5, to substantially reproduce the signal.

Figure 4B:
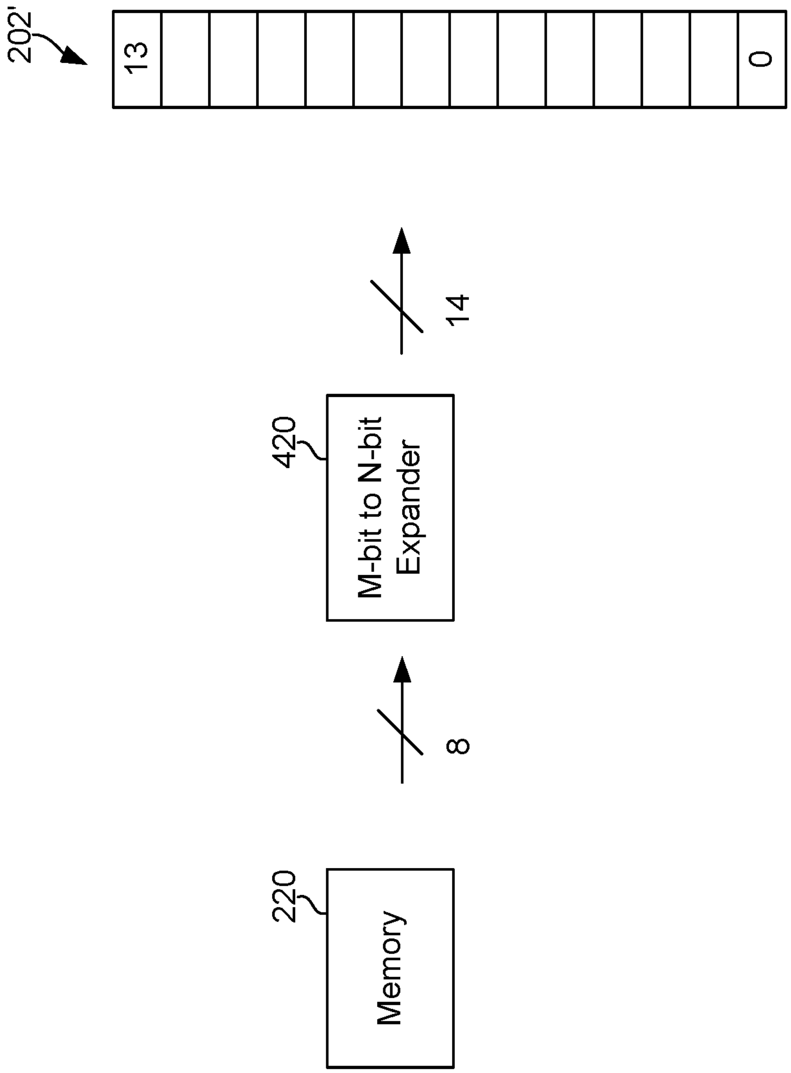
FIG. 4B is a high level illustration of how an expander can be used to expand an M-bit data value, that was stored in memory, to an expanded or reconstructed N-bit data value.

FIG. 4B is a high level illustration of how an expander 420 can be used to expand a compressed 8-bit data value (or more generally a compressed M-bit data value), that was stored in memory 120, to a 14-bit data value (or more generally, an N-bit data value). As shown in FIG. 4B, in accordance with certain embodiments, the compressed 8-bit data value stored in memory 220 (in FIG. 4A) is expanded using the expander 420 to thereby output an expanded value 202', which can also be referred to as a reproduced or reconstructed value 202'. The expander 420 can be implemented in either hardware or software, or a combination thereof, but preferably would be implemented in software to provide flexibility. Further, where the expander 420 is implemented by a non-implanted system or device, such as a clinical programmer, which receives uploaded data from the memory 220 of an IMD, the expander 420 does not have the same power and processing constraints as the compressor 420 (in FIG. 4A).

Figure 4C:
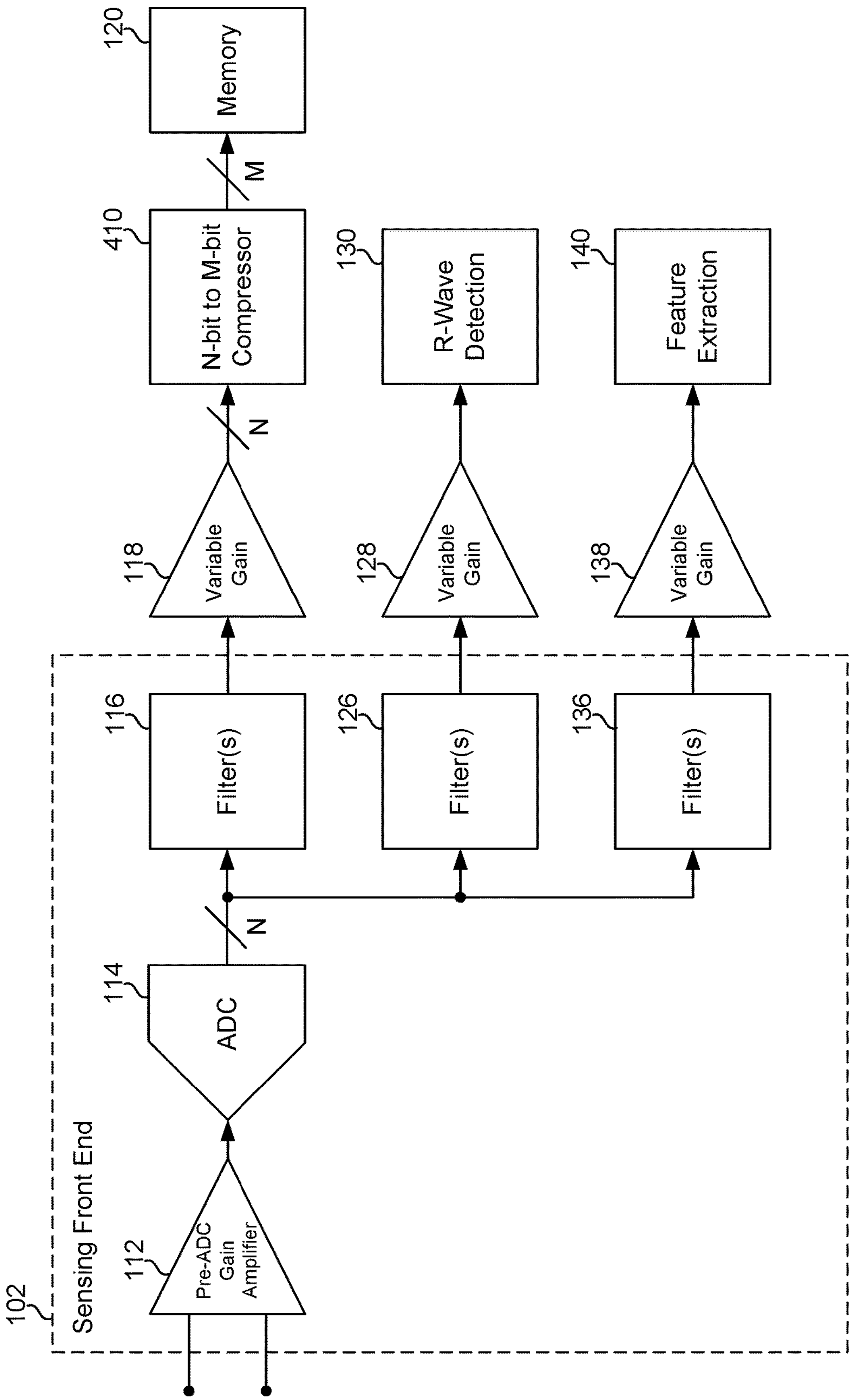
FIG. 4C illustrates how a compressor of an embodiment of the present technology can be added to the high level block diagram introduced in FIG. 1.

FIG. 4C illustrates how a compressor 410, of an embodiment of the present technology, can be added to the high level block diagram introduced in FIG. 1. Referring to just the upper signal path in FIG. 4C, a sensed analog biological signal is amplified by the amplifier 112 and then converted to an N-bit digital signal by the ADC 114, wherein the N-bit digital signal is made up of a plurality of N-bit data values indicative of the amplitude of the biological signal at various points in time. In other words, each N-bit data value is indicative of an amplitude of a biological signal at a point in time. In FIG. 4C, the N-bit data values, that are output by the ADC 114, are filtered in the digital domain by one or more filter(s) 116, and amplified in the digital domain by the variable gain amplifier 118. Still referring to FIG. 4C, in accordance with certain embodiments of the present technology, each of the filtered and amplified N-bit data values is compressed to an M-bit data value by the compressor 410 before being stored as M-bit data slices in the memory 120. It would also be possible to rearrange the order of the filter(s) 116, the amplifier 118 and the compressor, e.g., such that the compressor 410 is located between the ADC 114 and the filter(s) 116, or between the filter(s) 116 and the amplifier 118. It would also be possible to not include the filter(s) 116 and/or the amplifier 118. More generally, in accordance with certain embodiments of the present technology, each N-bit data value that is output by the ADC 114 (which can also be referred to as the N-bit ADC 114), or a filtered and/or amplified version of each N-bit data value output by the ADC 114, is compressed to an M-bit data value and thereafter stored as an M-bit data slice in the memory 120 so that the M-bit data value, or a filtered and/or amplified version thereof, can be expanded to a reproduced N-bit data value after being uploaded to a non-implanted device or system.

Figure 5:
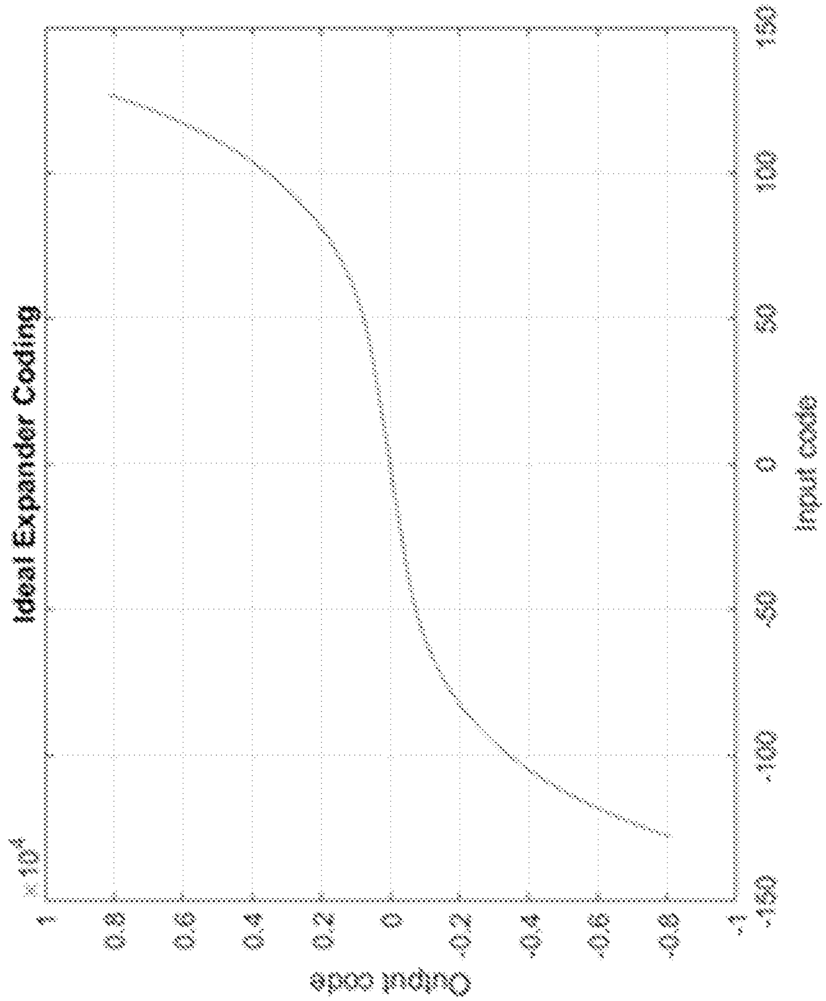
FIG. 5 illustrates an example expansion transformation curve that can be used to expand an M-bit data value to an N-bit data value.

FIG. 5 illustrates an example expansion transformation curve that can be used to expand an M-bit data value to an N-bit data value. In FIG. 5, the input code is an 8-bit code, which can be referred to more generally as a companded value, or a compressed value. Since an 8-bit code can represent 256 different values, where both negative and positive values are to be represented, the 8-bit input code can represent any value between −128 and +127. In FIG. 5, the output code is a 14-bit code, which can be referred to as a decoded value, an expanded value, a restored value, or a reconstructed value. Since a 14-bit code can represent 16,384 different values, where both negative and positive values are to be represented, the 14-bit output code can represent any value between −8192 and +8191.

Figure 6:
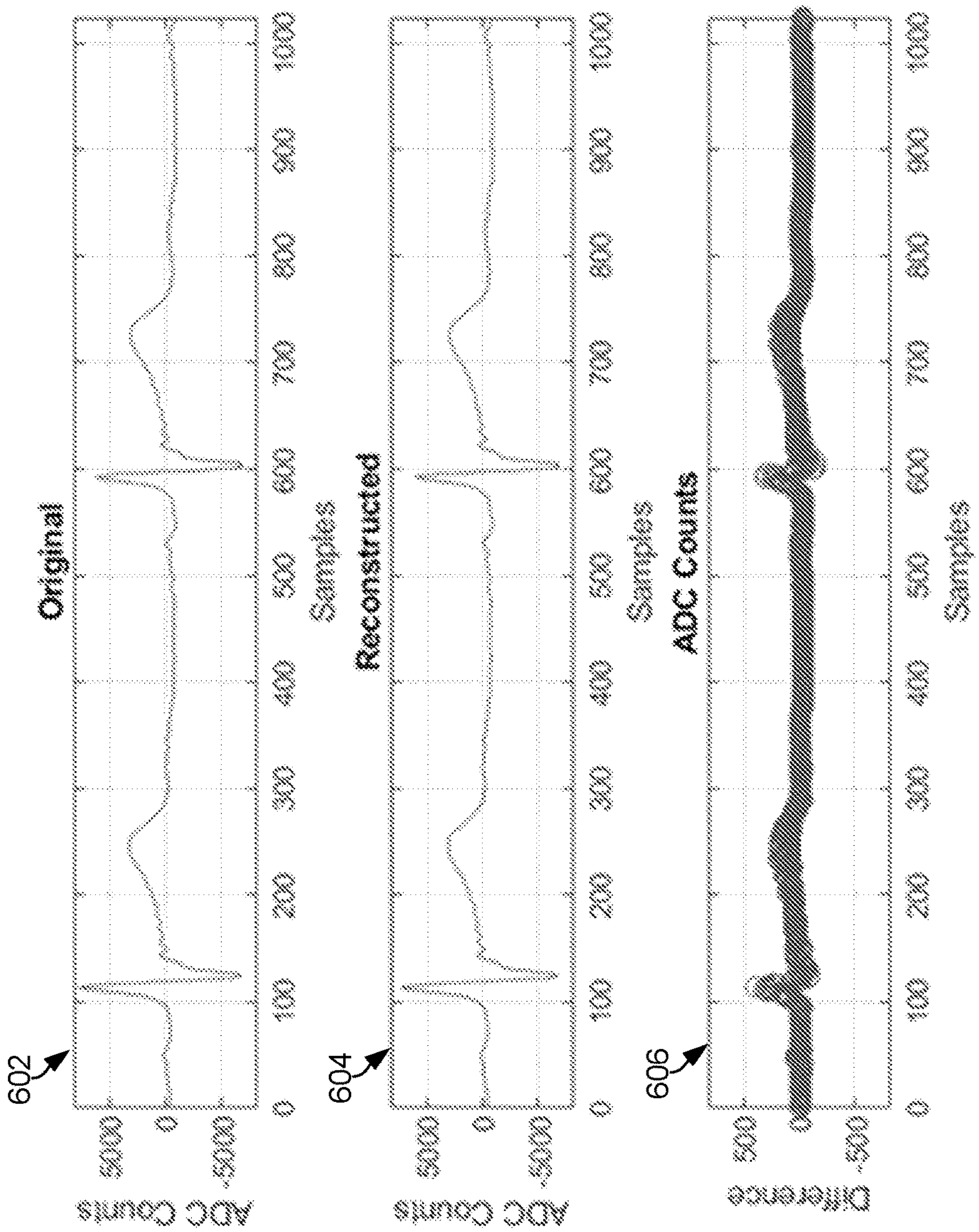
FIG. 6 illustrates an example of an original ECG/EGM waveform and a restored (aka reconstructed) ECG/EGM waveform, and also illustrates a graph of differences between the original waveform and the reconstructed waveform.

Since the non-implanted programmer (or other non-implanted device or system) has a large amount of unrestricted compute power, this operation is generally performed using an algorithm that is the reverse of the compression and is typically performed in software. Examples of an original ECG/EGM waveform 602 and a restored ECG/EGM waveform 604 (which can also be referred to as a reconstructed ECG/EGM waveform 604) are shown in FIG. 6. FIG. 6 also includes a graph 606 of differences between the original waveform 602 and the reconstructed waveform 604.

Because the data storage compression is achieved by selectively reducing precision of the signal level, this is a form of lossy dynamic range compression. In accordance with certain embodiments of the present technology, one or more lookup tables (LUTs) is/are stored in memory or registers of an IMD and used to perform the data compression, aka, the data companding or compansion. One or more further LUTs, or an algorithm, is/are used by a non-implanted programmer (or some other non-implanted device or system) to perform the data decompression, aka, the data expanding, or the data reconstruction. Depending on the parameters used for the compression and the decompression, the percent root mean square difference (PRD) for an ECG/EGM type waveform can be less than 4%. This value can vary greatly, depending upon the number of values in the LUT(s) used for the companding, and the type of transformation function and its associated parameters.

Where a transformation is symmetrical along the X-axis, only the positive section of the transformation needs to be computed. For compressing polarity-symmetrical data such as an audio signal, the companding curve's negative section is simply the sign-inverse version of its positive half. For polarity-asymmetric data such as an ECG/EGM signal, the optimal companding curve might not be symmetrical.

Figure 7:
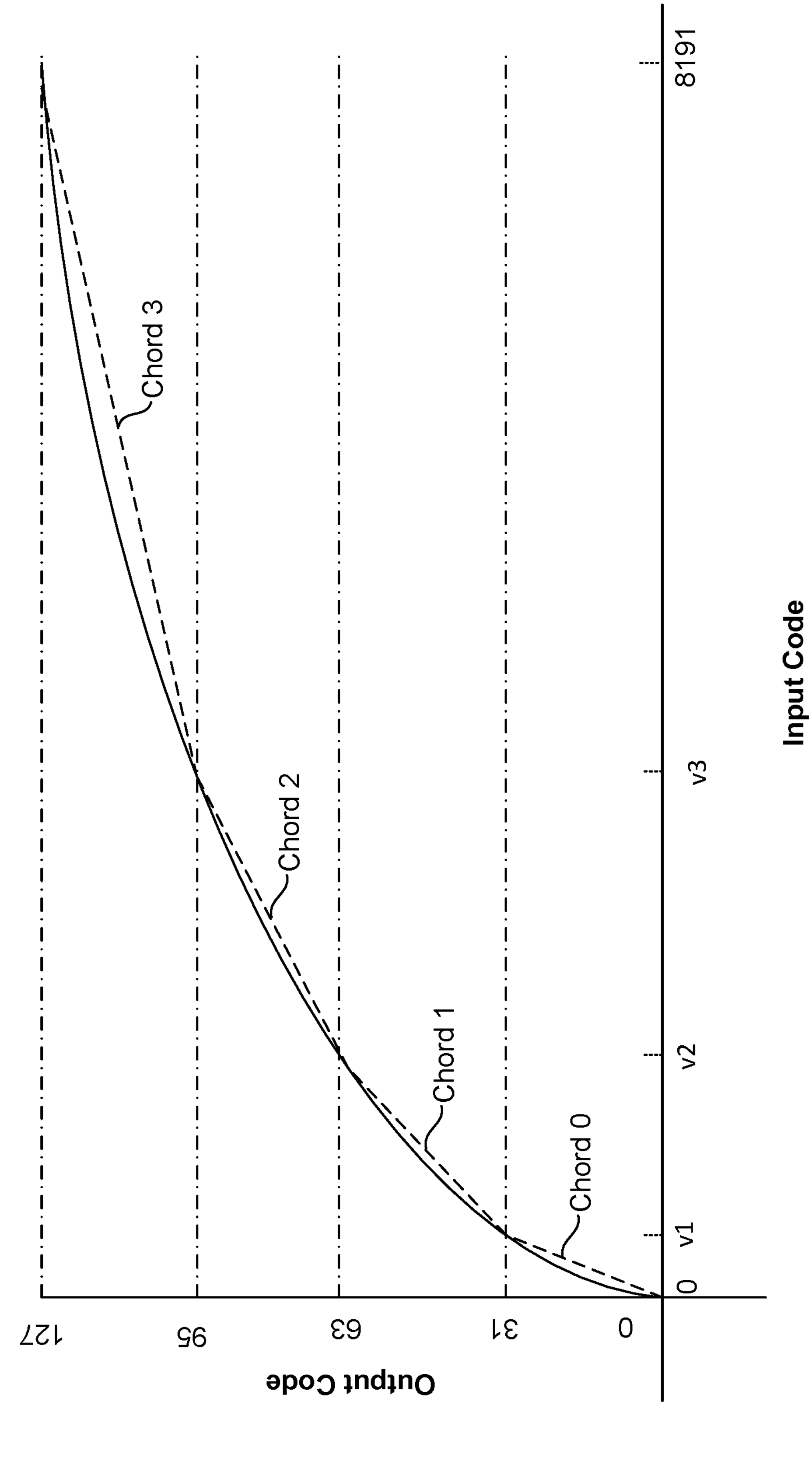
FIG. 7 illustrates how a companding curve can be split into a number of sections, which are called chords.

A companding curve is typically split into a number n of equal segments, called chords. Conventionally, once a signal value is known to be within a chord, a linear function is applied to the signal value to determine the output value. In general, the higher the number of segments (aka chords) the lower the error in signal reproduction at the expense of a more linear functions to compute. This operation is illustrated in FIG. 7 for an n of 4, with each of the n segments (4 segments in this example) estimated using a linear approximation. The n segments in FIG. 7, which can also be referred to as n chords, are labeled Chord 0, Chord 1, Chord 2, and Chord 3. In the example of FIG. 7, the Chord 0 is selected and used to compress the 14-bit input code when the magnitude thereof is between 0 and value_1 (v1), the Chord 1 is selected and used to compress the 14-bit input code when the magnitude thereof is equal to or greater than the v1 but less than v2, and the Chord 2 is selected and used to compress the 14-bit input code when the magnitude thereof is equal to or greater than the v2 but less than v3, and the Chord 3 is selected and used to compress the 14-bit input code when the magnitude thereof is between v3 and 8191. The values of v1, v2, and v3 are programmable and thereby changeable. In accordance with certain embodiments of the present technology, a companding curve need not be split into equal segments (aka chords), but rather, the different chords can have different sizes.

Figure 8:
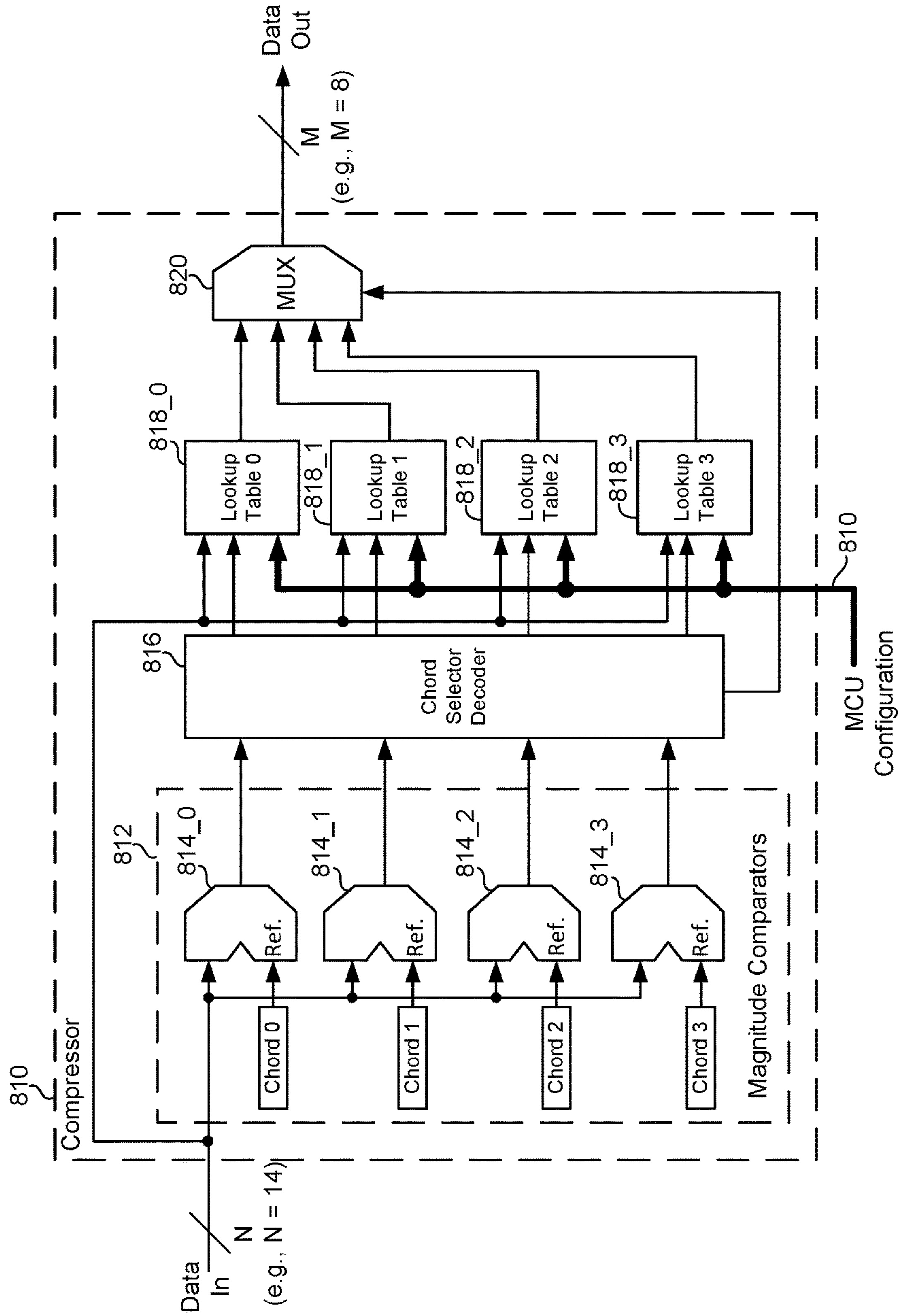
FIG. 8 illustrates an example implementation of the compressor introduced in FIG. 4A, according to an embodiment of the present technology.

In accordance with certain embodiments of the present technology, in order to efficiently implement this in a power constrained system, like an IMD, a non-linear logarithm is approximated using magnitude comparators and lookup tables (LUTs), as shown in FIG. 8, which is described below. Referring to FIG. 8, shown therein is a compressor 810 (e.g., 410 in FIG. 4C), according to an embodiment of the present technology. The compressor 810, which can also be referred to as a compander 810, is shown as including a magnitude comparators block 812, a chord selector decoder 816, a plurality of LUTs 818_0, 818_1, 818_2, and 818_3, and a multiplexer (MUX) 820. The LUTs 818_0, 818_1, 818_2, and 818_3 can be referred to collectively as the LUTs 818, or individually as an LUT 818. Such LUTs 818 can be stored in memory or registers of an IMD. Further, it is noted that one or more of the LUTs, which are stored in registers or memory of the IMD, can be updated by a non-implantable device, such as a clinical programmer, to thereby modify how N-bit data values that are output by an ADC are compressed to M-bit data values that are stored in the memory.

The magnitude comparators block 812 is shown as including a plurality of digital comparators 814_0, 814_1, 814_2, and 814_3, which can be referred to collectively as the digital comparators 814, or individually as a digital comparator 814. The digital comparators 814 can also be referred to magnitude comparators 814, or more succinctly as comparators 814. Still referring to FIG. 8, each of the comparators 814 includes a data input, a reference (ref.) input, and an output. The data input of each of the comparators 814 receives the same data input signal, which at any instance in time is an N-bit digital data value, e.g., received from an ADC within an IMD (potentially after the N-bit data value has been filtered and/or amplified). In accordance with certain embodiments, the reference input of each of the comparators 814 receives a respective chord value that corresponds to the upper end of the range of one of the n chords, where n in this example is 4. More generally, the reference values correspond to boundaries of a plurality of magnitude ranges. For example, the Chord 0 value that is provided to reference input of the comparator 814_0 can specify the upper end of one chord, the Chord 1 value that is provided to the reference input of the comparator 814_1 can specify the upper end of another chord, the Chord 2 value that is provided to the reference input of the comparator 814_2 can specify the upper end of still another chord, and the Chord 3 value that is provided to the reference input of the comparator 814_3 can specify the upper end of a further chord. In certain embodiments, each of the magnitude comparators 814 has three possible outputs, which can indicate whether the input value is less than the reference value, equal to the reference value, or greater than the reference value. In alternative embodiments, each of the magnitude comparators 814 has only two possible outputs, which can indicate whether the input value is less than the reference value, or whether the input value is greater than or equal to the reference value. In certain embodiments, the chord values (Chord 0, Chord 1, Chord 2, and Chord 3) that are provided to the reference inputs of the comparators 814 can be stored, e.g., in programmable registers of an IMD, and can be reprogrammed as desired. Further, the contents of the LUTs 818 can be reprogrammed as desired by an external device or system.

The outputs of the magnitude comparators block 812, or more specifically the comparators 814 thereof, are provided to the chord selector decoder 816. The chord selector decoder 816 decodes the various possible combinations of outputs from the comparators 814 to identify which chord the data input value is located within, and based thereon, selects which one of the LUTs 818 should be used to produce a data output based on the data input. In certain embodiments, the output of the magnitude comparators block 812 is thermometer coded, and the chord selector 816 functions as a thermometer decoder. Other variations are also possible, and within the scope of the embodiments described herein. The chord selector decoder 816 is also shown as selecting which input to the MUX 820 is provided at the output of the MUX 820 for storing in memory (e.g., 220) of an IMD. For example, if the chord selector decoder 816 determines that a data input value is within the Chord 2, and selects the LUT 818_2 to use, then the output of the LUT 818_2 that is provided to one of the inputs of the MUX 820 is passed through and output by the MUX 820.

In accordance with certain embodiments, an input to the selected LUT 818, which input is used to determine which stored value should be output from the selected LUT 818, is the N-bit data value that is provided to the compressor 810, or more likely, just a segment thereof that is less than the entire N-bits. The specific segment that is provided to an input of a selected LUT 818 can depend on the specific LUT 818 that is selected. In accordance with certain embodiments, each LUT only works on a fraction of the total number the N-bits. For example, if there are four LUTs 818, and the chord selector decoder 816 evenly divides the input by powers of 2, then only the two MSBs of the N-bits are used by to determine which of the four LUTs 818 is selected, and the input to each LUT is the lower N−2 bits (i.e., the N−2 LSBs). For a more specific example, the LUT 818_0_is selected when the MSBs are 00, the LUT 818_1_is selected when the MSBs are 01, the LUT 818_2_is selected when the MSBs are 10, and the LUT 818_3_is selected when the MSBs are 11. For another example, if there are eight LUTs 818, and the chord selector decoder 816 evenly divides the input by powers of 2, then the three MSBs of the N-bits are used by to determine which of the eight LUTs 818 is selected, and the input to each LUT is the lower N−3 bits (i.e., the N−3 LSBs). In the above examples, the chord selector decoder 816 evenly divides its input by powers of 2, which enables simple decoding of the input to the chord selector decoder 816, which would eliminate the need for the magnitude comparators 812, by simply providing a predetermined number of the MSBs of the N-bits to the chord selector decoder 816. In the embodiment shown in FIG. 8, the chord selector decoder 816 does not need to evenly divide its input by powers of 2, but rather, can choose at any arbitrary point along its transformation curve to choose a chord and not be restricted to a power of 2, providing for more flexibility and optimization. Other variations are also possible and within the scope of the embodiments described herein.

Figure 9:
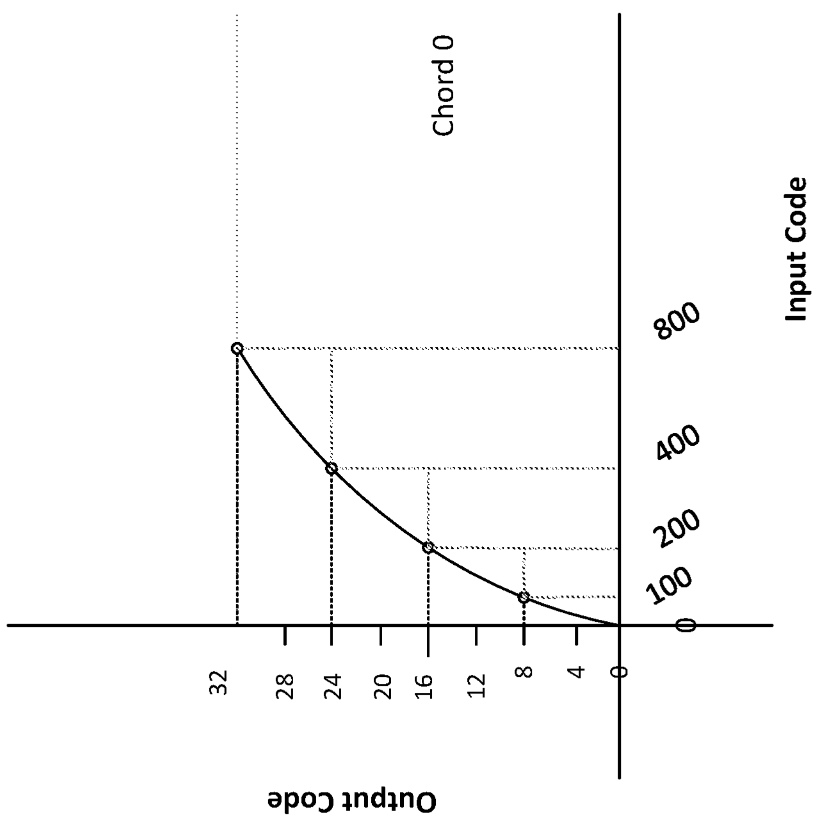
FIG. 9 illustrates an example implementation of one of the chords introduced in FIG. 7.

Using a LUT for each chord further reduces power consumption, compared to if an algorithm were instead used for each chord. In accordance with certain embodiments, each of the LUTs is used to map a sub-range of input values to a single output value for encoding. The number of values to decode within a chord is chosen as a trade-off between look-up-table size and a desired maximum allowable error in reproduction. A simple example, for illustration of this process, is shown in FIG. 9 for only four entries of lookup for a chord. More specifically, FIG. 9 illustrates an example implementation of the Chord 0 introduced in FIG. 7, wherein Chord 0 is selected and used where a magnitude of an input code (e.g., an N-bit data value) is between 0 and v1, and v1 is equal to 800 in this example. Referring to the example LUT 912 shown at the right in FIG. 9, the magnitude range associated with the Chord 0 is from 0 to 800, and that magnitude range is divided into four sub-ranges, including a subrange from 0 to 100, a subrange from 101 to 200, a subrange from 201 to 400, and a subrange from 401 to 800. Using the LUT 912 for Chord 0, whenever an input code is within the subrange from 0 to 100 the output code will be 0, whenever an input code is within the subrange from 101 to 200 the output code will be 8, whenever an input code is within the subrange from 201 to 400 the output code will be 16, and whenever an input code is within the subrange from 401 to 800 the output code will be 24. This is just an example, which is not intended to be limiting.

Also note that the transformation values for each chord are configurable and can be reconfigured on a device by device basis if desired. Any transformation curve can be implemented, linear or non-linear. Unlike the digital approximation of a non-linear logarithmic companding curve implemented using conventional A-law and p-law compression functions, these embodiments of the present technology enable implementation of any arbitrary companding curve—distributing the highest signal fidelity to the signal levels wherever it is most desired.

Figure 10:
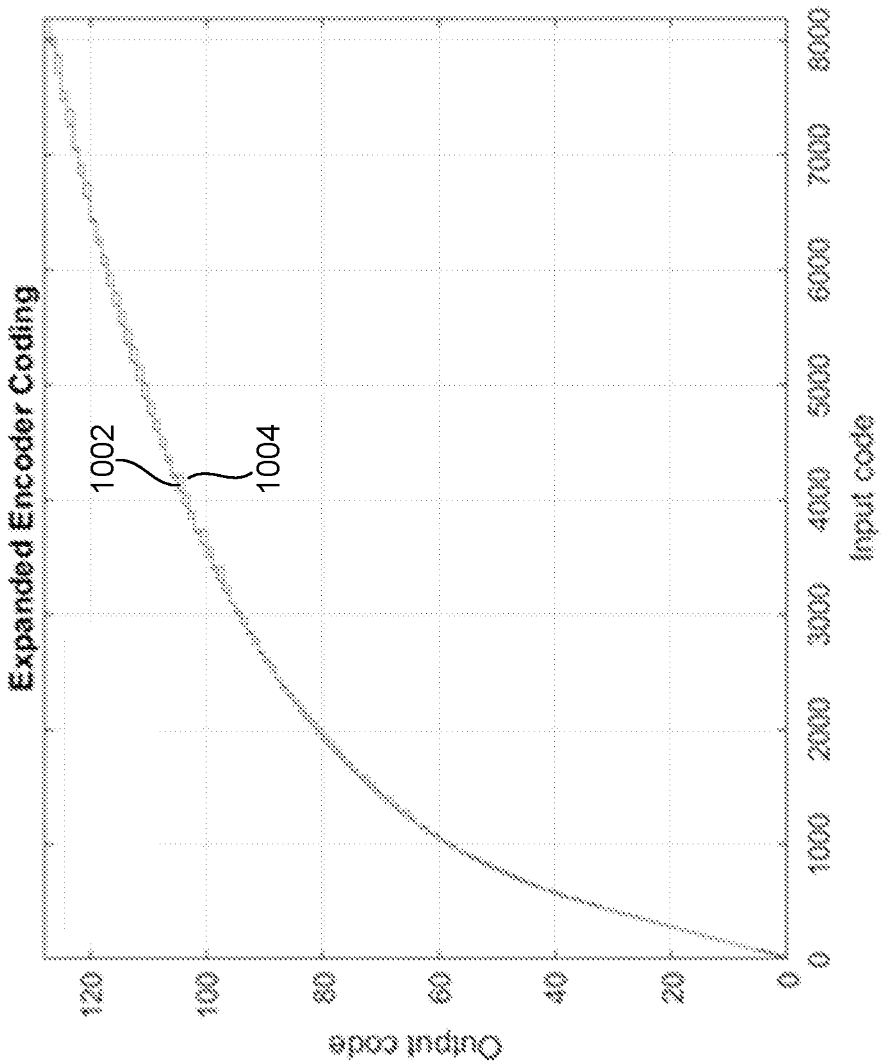
FIG. 10 illustrates the difference between an expanded encoder coding for ideal encoding, and an expanded encoder coding for actual encoding using an embodiment of the present technology.

The difference between the ideal and actual implementation for the positive half of the compression is shown in FIG. 10, wherein the curve 1002 is the expanded encoder coding for ideal encoding, and the curve 1004 is the expanded encoder coding for actual encoding using an embodiment of the present technology. This is shown for 4 chords and 32 entries for each chord (in contrast to the 4 entries for each chord that is shown in the example described above with reference to FIG. 9). In this example case the least mean squared error between the original and reconstructed waveform is less than 1%. The use of LUTs to “bend” each chord—rather than use of a linear approximation equation for each chord—avoids distorting the signal as its level transitions between adjacent chords.

Figure 11:
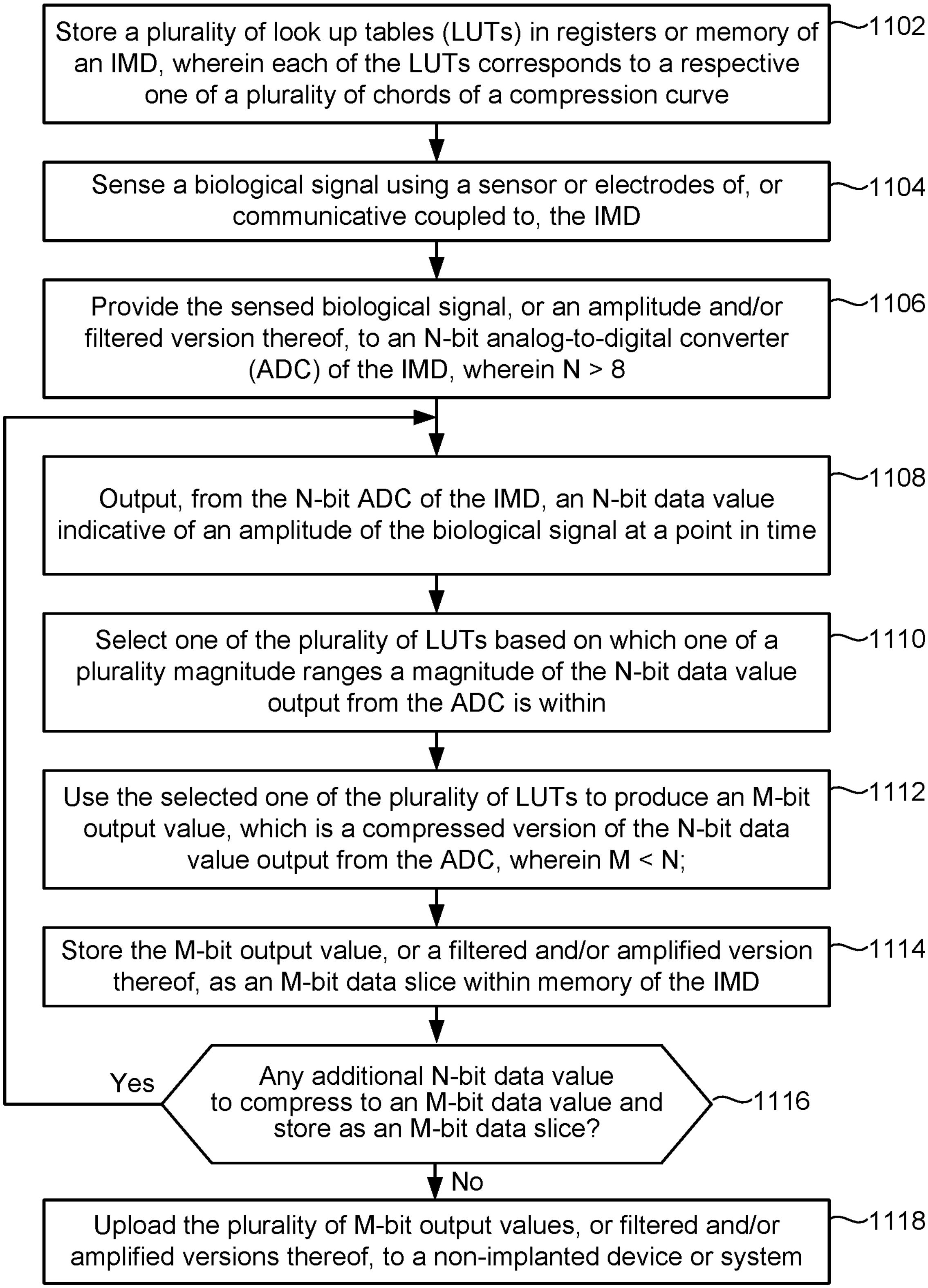
FIG. 11 is a high level flow diagram used to summarize embodiments of the present technology that utilize LUTs to efficiently store data for a sensed biological signal.

The high level flow diagram of FIG. 11 will now be used to summarize the embodiments of the present technology, which were introduced above, that utilize lookup tables (LUTs) to efficiently store data for a sensed biological signal. The IMD that performs one of the methods summarized with reference to FIG. 11 can be, e.g., a pacemaker coupled to one or more transvenous leads, a leadless pacemaker, an insertable cardiac monitor (ICM), or an implantable cardioverter defibrillator (ICD), but is not limited thereto.

Referring to FIG. 11, step 1102 involves storing a plurality of look up tables (LUTs) in registers or memory of an implantable medical device (IMD), wherein each of the LUTs corresponds to a respective one of a plurality of chords of a compression curve. In accordance with certain embodiments, each LUT, of the plurality of LUTs, has a respective different output value for each of a plurality of different sub-ranges of magnitudes, such that the LUT is used to produce a same one of a plurality of different output values for a plurality of different input values that are within a same one of the sub-ranges of magnitudes. Referring briefly back to FIG. 9, the table 912 shown at the right is an example of a LUT for the Chord 0.

Referring again to FIG. 11, step 1104 involves sensing a biological signal using a sensor or electrodes of, or communicatively coupled to, the IMD. The biological signal can be, e.g., an EGM or ECG signal indicative of cardiac electrical activity that is sensed using electrodes of the IMD, or communicatively coupled to the IMD. Alternatively, the biological signal can be a photoplethysmography (PPG) signal indicative of cardiac mechanical activity that is sensed using an optical sensor of the IMD, or communicatively coupled to the IMD. Alternatively, the biological signal can be an impedance plethysmography (IPG) signal indicative of cardiac mechanical activity that is sensed using electrodes of the IMD, or communicatively coupled to the IMD. The biological signal can alternatively be a heart sound signal, any one of various different types of pressure signals, and/or the like. Examples of other biological signals that can be sensed at step 1104 include a signal indicative of body temperature, a signal indicative of motion, a signal indicative of blood pressure, and a cardiogenic impedance signal. The above mentioned examples of biological signals are not intended to be limiting or all encompassing.

Step 1106 involves providing the sensed biological signal, or an amplitude and/or filtered version thereof, to an N-bit analog-to-digital converter (ADC) of the IMD, wherein N>8, so that the sensed biological signal (or an amplitude and/or filtered version thereof) is converted to N-bit data values by the N-bit ADC. Step 1108 involves outputting, from the N-bit ADC of the IMD, an N-bit data value indicative of an amplitude of the biological signal at a point in time. The ADC 114 shown in and described above with reference to FIGS. 1 and 4C is an example of the N-bit ADC that can used at steps 1106 and 1108. What occurs at steps 1106 and 1108, over time, can be more generally described as converting an analog signal, which corresponds to a sensed biological signal, to a digital signal that comprises a plurality of N-bit data values, wherein N>8.

Step 1110 involves selecting one of the plurality of LUTs based on which one of a plurality magnitude ranges a magnitude of the N-bit data value output from the ADC is within. For example, referring briefly back to FIG. 7, if an N-bit data value is between 0 and value 1 (v1), and thus corresponds to Chord 0, then the LUT corresponding to Chord 0 is selected. If the N-bit data value is between v1 and the value 2 (v2), and thus corresponds to Chord 1, then the LUT corresponding to Chord 1 is selected. If the N-bit data value is between v2 and the value 3 (v3), and thus corresponds to Chord 2, then the LUT corresponding to Chord 2 is selected. If the N-bit data value is between v3 and the maximum value (8191 in this example), and thus corresponds to Chord 3, then the LUT corresponding to Chord 3 is selected. Referring briefly back to FIG. 8, in accordance with certain embodiments, the selecting at step 1110 can be performed using the magnitude comparators block 812 and the chord selector decoder 816 shown in FIG. 8, but is not limited thereto. As can be appreciated from FIG. 8, and the above discussion thereof, at any given time, each of the magnitude comparators 812 compares a magnitude of a same one of the N-bit data values to a different one of a plurality of reference values (labeled Chord 0, Chord 1, Chord 2, and Chord 3 in FIG. 8) that correspond to boundaries of the plurality of magnitude ranges. As can be appreciated from FIG. 8, and the above discussion thereof, the decoder 816 receives the outputs of the magnitude comparators 814 (of the magnitude comparators block 812) and selects one of the plurality of LUTs 818 by decoding the outputs of the magnitude comparators 814. In certain embodiments, step 1110 can be performed without any magnitude comparators 812, e.g., by selecting one of the plurality of LUTs based on the 2 MSBs (or some other number of MSBs) of the N-bit data value, and more specifically, by providing the 2 MSBs (or some other number of MSBs) directly to the chord selector decoder 816 shown in FIG. 8, which is a specific implementation of the selecting (at step 1110) one of the plurality of LUTs based on which one of a plurality magnitude ranges a magnitude of the N-bit data value output from the ADC is within.

Referring again to FIG. 11, step 1112 involves using the selected one of the plurality of LUTs to produce an M-bit data value, which is a compressed version of the N-bit data value output from the ADC, wherein M<N. In accordance with certain embodiments, N is greater than 8 and less than 16 (i.e., 16>N>8), and M=8. In the specific examples described herein, it was assumed that N=14, but embodiments of the present technology are not limited to that value for N. Similarly, while it is likely the M=8, it is possible for M to have some other value, while still being within the scope of the embodiments described herein, so long as M<N.

Step 1114 involves storing the M-bit data value, or a filtered and/or amplified version thereof, as an M-bit data slice within memory of the IMD, so that the M-bit data value, or a filtered and/or amplified version thereof, can be expanded to a reproduced N-bit data value after being uploaded to a non-implanted device or system.

At step 1116 there is a determination of whether there are one or more additional N-bit data values that need to be compressed to M-bit data values so that they can be stored as M-bit data slices in memory. If the answer to the determination at step 1116 is Yes, then flow returns to step 1108, and steps 1108-1114 are repeated for another N-bit data value. More generally, the outputting at step 1108, selecting at step 1110, using at step 1112, and storing at step 1114 may be repeated for a plurality of additional N-bit data values indicative of amplitudes of the biological signal at a plurality of additional points in time, so that a plurality of M-bit data values, or filtered and/or amplified versions thereof, are stored as a plurality of M-bit data slices within the memory of the IMD.

If the answer to the determination at step 1118 is No, then flow goes to step 1118. Step 1118 involves uploading the plurality of M-bit data values, or filtered and/or amplified versions thereof, to a non-implanted device or system so that the M-bit data values, or filtered and/or amplified versions thereof, can be expanded to a provide a plurality of N-bit reproduced data values, by the non-implanted device or system, and so that the N-bit reproduced values can be used by the non-implanted device or system to generate a reproduced version of the biological signal. There may, or may not be, a relatively long period of time between when step 1116 occurs and when step 1118 occurs. For example, step 1118 may only occur from time to time, when a patient visits a medical facility and a session is initiated between a clinical programmer and the IMD using RF communication, inductive communication, or conductive communication, but not limited thereto. It is also possible that step 1118 is performed using a bedside monitor, or some other non-implantable device at a patient's home. After the M-bit data values have been uploaded to a non-implanted device or system, the non-implanted device or system can decompress the uploaded M-bit data values to N-bit data values so that a reconstructed biological signal can be displayed to a medical practitioner, and/or analyzed using one or more processors and/or other types of circuitry. LUTs, which are essentially the inverse of the LUTs stored at step 1102 and used at step 1112, can be used to perform the decompression of the M-bit data values to N-bit data values. Alternatively, one or more equations, which are stored in memory of the non-implantable device or system, and which can be executed using one or more processors of the non-implantable device or system, can be used to perform the decompression of the M-bit data values to N-bit data values. Such decompression of the M-bit data values to N-bit data values can also be referred to as expansion, reconstruction, or reproduction of M-bit data values to N-bit data values.

As explained above, embodiments of the present technology, described herein, enable wide dynamic range and high resolution biological signals, such as ECG or EGM signals, and more specifically, data indicative thereof, to be efficiently stored in memory of an IMD. The IMD can store this biological signal data based on various triggers, e.g., in response an arrhythmia detection, or some other triggering event. The biological signal data can alternatively, or additionally, be periodically stored, e.g., once per day, one per hour, or the like. When needed, the data can be uploaded from the implantable device to a programmer. The programmer, or another device or system that is communicatively coupled to the programmer, can then expand the biological signal data such that wide dynamic range and high resolution biological signals can be substantially reconstructed or reproduced, and then displayed and/or otherwise analyzed by a clinician.

An example of such an IMD is described below with reference to FIG. 12. Thereafter, the efficiently stored data can be uploaded to a non-implanted device or system and expanded such that the wide dynamic range and high resolution biological signals can substantially reconstructed or reproduced, and then displayed and/or otherwise analyzed. Where the IMD is battery powered, as it typically the case, and is small in size, the IMD is limited power and processing resources that are important to conserve.

EXAMPLE IMD

Figure 12:
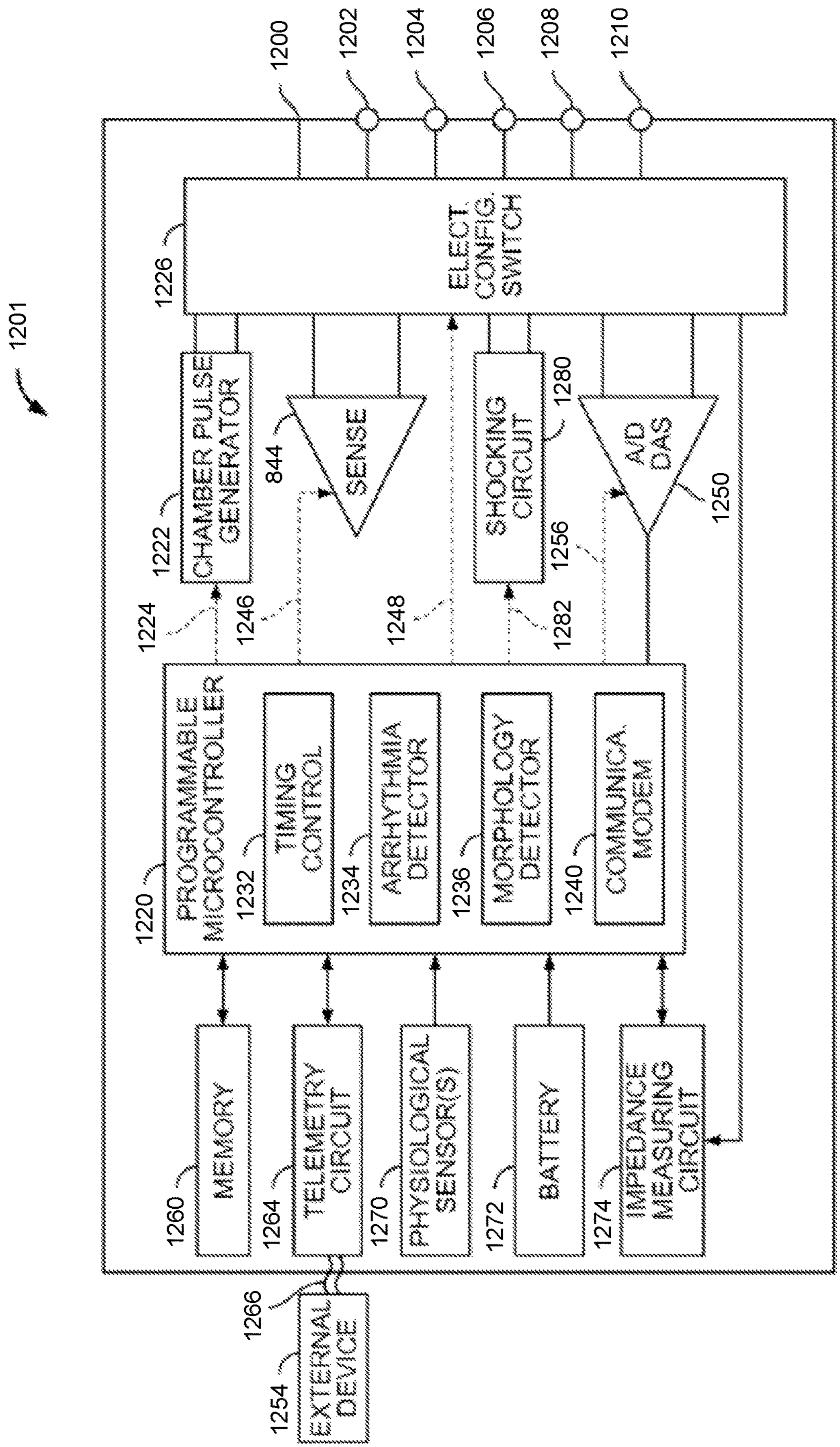
FIG. 12 is a high level block diagram of an example IMD that can implement certain embodiments of the present technology.

FIG. 12 shows a block diagram of one embodiment of an IMD (e.g., a pacemaker or ICD) 1201 that is implanted into the patient in accordance with certain embodiments herein. IMD 1201 may be implemented as a full-function biventricular pacemaker, equipped with both atrial and ventricular sensing and pacing circuitry for four chamber sensing and stimulation therapy (including both pacing and shock treatment). Optionally, IMD 1201 may provide full-function cardiac resynchronization therapy. Alternatively, IMD 1201 may be implemented with a reduced set of functions and components. For instance, the IMD may be implemented without ventricular sensing and pacing. Indeed, the IMD can be an ICM that performs monitoring but not therapy.

IMD 1201 has a housing 1200 to hold the electronic/computing components. Housing 1200 (which is often referred to as the "can", "case", "encasing", or "case electrode") may be programmably selected to act as the return electrode for certain stimulus modes. Housing 1200 may further include a connector (not shown) with a plurality of terminals 1202, 1204, 1206, 1208, and 1210. The terminals may be connected to electrodes that are located in various locations on housing 1200 or elsewhere within and about the heart. IMD 1201 includes a programmable microcontroller 1220 that controls various operations of IMD 1201, including cardiac monitoring and stimulation therapy. Microcontroller 1220 includes a microprocessor (or equivalent control circuitry), RAM and/or ROM memory, logic and timing circuitry, state machine circuitry, and I/O circuitry. While not specifically shown in FIG. 12, the microcontroller 1220 can include registers, and such registers can be used to store the LUTs 818 introduced above in FIG. 8. Alternatively, the LUTs 818 can be stored in the memory 1260.

IMD 1201 further includes a pulse generator 1222 that generates stimulation pulses for delivery by one or more electrodes coupled thereto. Pulse generator 1222 is controlled by microcontroller 1220 via control signal 1224. Pulse generator 1222 may be coupled to the select electrode(s) via an electrode configuration switch 1226, which includes multiple switches for connecting the desired electrodes to the appropriate I/O circuits, thereby facilitating electrode programmability. Switch 1226 is controlled by a control signal 1228 from microcontroller 1220.

In the embodiment of FIG. 12, a single pulse generator 1222 is illustrated. Optionally, the IMD may include multiple pulse generators, similar to pulse generator 1222, where each pulse generator is coupled to one or more electrodes and controlled by microcontroller 1220 to deliver select stimulus pulse(s) to the corresponding one or more electrodes.

Microcontroller 1220 is illustrated as including timing control circuitry 1232 to control the timing of the stimulation pulses (e.g., pacing rate, atrio-ventricular (AV) delay, atrial interconduction (A-A) delay, or ventricular interconduction (V-V) delay, etc.). Timing control circuitry 1232 may also be used for the timing of refractory periods, blanking intervals, noise detection windows, evoked response windows, alert intervals, marker channel timing, and so on. Microcontroller 1220 also has an arrhythmia detector 1234 for detecting arrhythmia conditions and a morphology detector 1236. Although not shown, the microcontroller 1220 may further include other dedicated circuitry and/or firmware/software components that assist in monitoring various conditions of the patient's heart and managing pacing therapies.

IMD 1201 is further equipped with a communication modem (modulator/demodulator) 1240 to enable wireless communication with an external device (e.g., 854), and/or with another implantable device, using radio frequency (RF) communication, inductive communication, or conductive communication, but not limited thereto. Modem 1240 may be implemented in hardware as part of microcontroller 1220, or as software/firmware instructions programmed into and executed by microcontroller 1220. Alternatively, modem 1240 may reside separately from the microcontroller as a standalone component. In certain embodiments, the modem 1240 includes both a conductive communication transceiver and an RF communication transceiver. While not specifically shown in FIG. 12, such an RF communication transceiver can be coupled to an antenna that enables RF communication signals to be transmitted and received for the purpose of transmitting and receiving messages to and from another IMD.

IMD 1201 includes a sensing circuit 1244 selectively coupled to one or more electrodes, that perform sensing operations, through switch 1226 to detect the presence of cardiac activity in the right chambers of the heart. Sensing circuit 1244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1226 determines the sensing polarity of the cardiac signal by selectively closing the appropriate switches. In this way, the clinician may program the sensing polarity independent of the stimulation polarity.

The output of sensing circuit 1244 is connected to microcontroller 1220 which, in turn, triggers or inhibits the pulse generator 1222 in response to the presence or absence of cardiac activity. Sensing circuit 1244 receives a control signal 1246 from microcontroller 1220 for purposes of controlling the gain, threshold, polarization charge removal circuitry (not shown), and the timing of any blocking circuitry (not shown) coupled to the inputs of the sensing circuitry.

In the embodiment of FIG. 12, a single sensing circuit 1244 is illustrated. Optionally, the IMD may include multiple sensing circuits, similar to sensing circuit 1244, where each sensing circuit is coupled to one or more electrodes and controlled by microcontroller 1220 to sense electrical activity detected at the corresponding one or more electrodes. Sensing circuit 1244 may operate in a unipolar sensing configuration or in a bipolar sensing configuration.

IMD 1201 further includes an analog-to-digital (ADC) data acquisition system (DAS) 1250 coupled to one or more electrodes via switch 1226 to sample cardiac signals across any pair of desired electrodes. Data acquisition system 1250 is configured to acquire EGM or ECG signals, convert the raw analog data into digital data, and store the digital data for later processing and/or telemetric transmission to an external device 1254 (e.g., a programmer, local transceiver, or a diagnostic system analyzer). Data acquisition system 1250 is controlled by a control signal 1256 from the microcontroller 1220.

In accordance with certain embodiments, the ADC 1250 is an N-bit ADC, and an embodiment of the present technology is used to compress N-bit data values that are output by the ADC 1250 to M-bit data values that are stored as M-bit data slices within memory 1260 of the IMD. Accordingly, a compressor 410, according to an embodiment of the present technology, can be located between the ADC 1250 and the memory 1260. One or more filters and/or amplifiers may also be located downstream of the ADC 1250, such that the EGM (or ECG) signal that is provided to an input of the ADC 1250 is filtered and/or amplified in the analog domain, before being converted to N-bit data values. Additionally, or alternatively, one or more filters and/or amplifiers can be located upstream of the ADC 1250, so that the N-bit data values output by the ADC 1250 can be filtered and/or amplified after being compressed, or before being compressed to M-bit data slices, prior to being saved in the memory 1260 as M-bit data slices.

Microcontroller 1220 can be coupled to the memory 1260 by a suitable data/address bus. The programmable operating parameters used by microcontroller 1220 are stored in memory 1260 and used to customize the operation of IMD 1201 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of IMD 1201 may be non-invasively programmed into memory 1260 through a telemetry circuit 1264 in telemetric communication via communication link 1266 with external device 1254. Telemetry circuit 1264 allows intracardiac electrograms and status information relating to the operation of IMD 1201 (as contained in microcontroller 1220 or memory 1260) to be sent to external device 1254 through communication link 1266.

IMD 1201 can further include magnet detection circuitry (not shown), coupled to microcontroller 1220, to detect when a magnet is placed over the unit. A magnet may be used by a clinician to perform various test functions of IMD 1201 and/or to signal microcontroller 1220 that external device 1254 is in place to receive or transmit data to microcontroller 1220 through telemetry circuits 1264.

IMD 1201 can further include one or more physiological sensors 1270. Such sensors are commonly referred to as "rate-responsive" sensors because they are typically used to adjust pacing stimulation rates according to the exercise state of the patient. However, physiological sensor 1270 may further be used to detect changes in cardiac output, changes in the physiological condition of the heart, or diurnal changes in activity (e.g., detecting sleep and wake states). Signals generated by physiological sensors 1270 are passed to microcontroller 1220 for analysis. Microcontroller 1220 responds by adjusting the various pacing parameters (such as rate, AV Delay, V-V Delay, etc.) at which the atrial and ventricular pacing pulses are administered. While shown as being included within IMD 1201, physiological sensor(s) 1270 may be external to IMD 1201, yet still be implanted within or carried by the patient. Examples of physiologic sensors might include sensors that, for example, sense respiration rate, pH of blood, ventricular gradient, activity, position/posture, minute ventilation (MV), and so forth.

A battery 1272 provides operating power to all of the components in IMD 1201. Battery 1272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 1272 also desirably has a predictable discharge characteristic so that elective replacement time can be detected. As one example, IMD 1201 employs lithium/silver vanadium oxide batteries.

IMD 1201 further includes an impedance measuring circuit 1274, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1274 is coupled to switch 1226 so that any desired electrode may be used. In this embodiment IMD 701 further includes a shocking circuit 1280 coupled to microcontroller 720 by a data/address bus 1282.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are example embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. For use by an implantable medical device (IMD), a method for efficiently storing data for a sensed biological signal, the method comprising:

providing the sensed biological signal, or an amplified and/or filtered version thereof, to an N-bit analog-to-digital converter (ADC) of the IMD, wherein N>8;

outputting, from the N-bit ADC of the IMD, an N-bit data value indicative of an amplitude of the sensed biological signal at a point in time;

selecting one of a plurality of chords of a compression curve based on which one of a plurality magnitude ranges a magnitude of the N-bit data value output from the ADC is within;

using the selected one of the plurality of chords of the compression curve to produce an M-bit data value, which is a compressed version of the N-bit data value output from the ADC, wherein M<N; and storing the M-bit data value, or a filtered and/or amplified version thereof, as an M-bit data slice within memory of the IMD, so that the M-bit data value, or the filtered and/or amplified version thereof, can be expanded to a reproduced N-bit data value after being uploaded to a non-implanted device or system.

2. The method of claim 1, further comprising:

storing a plurality of look up tables (LUTs) in registers or memory of the IMD, wherein each of the LUTs corresponds to a respective one of the plurality of chords of the compression curve;

wherein the selecting one of the plurality of chords of the compression curve, comprises selecting one of the plurality of LUTs based on which one of the plurality magnitude ranges the magnitude of the N-bit data value output from the ADC is within; and wherein the using the selected one of the plurality of chords of the compression curve to produce the M-bit data value, comprises using the selected one of the plurality of LUTs to produce the M-bit data value.

3. The method of claim 2, wherein:

each LUT, of the plurality of LUTs, has a respective different output value for each of a plurality of different sub-ranges of magnitudes, such that the LUT is used to produce a same one of a plurality of different output values for a plurality of different input values that are within a same one of the sub-ranges of magnitudes.

4. The method of claim 2, further comprising:

updating one or more of the LUTs stored in the registers or memory to thereby modify how further N-bit data values that are output by the ADC are compressed to further M-bit data values that are stored in the memory.

5. The method of claim 1, further comprising:

repeating the outputting, the selecting, the using, and the storing for a plurality of additional N-bit data values indicative of amplitudes of the biological signal at a plurality of additional points in time, so that a plurality of M-bit data values, or filtered and/or amplified versions thereof, are stored as a plurality of M-bit data slices within the memory of the IMD.

6. The method of claim 5, wherein:

the selecting is performed using a plurality of magnitude comparators and a decoder that receives outputs of the magnitude comparators;

at any given time, each of the magnitude comparators compares a magnitude of a same one of the N-bit data values to a different one of a plurality of reference values that correspond to boundaries of the plurality of magnitude ranges; and the decoder receives the outputs of the magnitude comparators and selects one of the plurality of chords by decoding the outputs of the magnitude comparators.

7. The method of claim 5, further comprising:

uploading the plurality of M-bit data values, or filtered and/or amplified versions thereof, that are stored in the memory of the IMD to a non-implanted device or system so that the M-bit data values, or filtered and/or amplified versions thereof, can be expanded to provide a plurality of N-bit reproduced data values, by the non-implanted device or system, and so that the N-bit reproduced values can be used by the non-implanted device or system to generate a reproduced version of the biological signal.

8. The method of claim 1, further comprising:

sensing the biological signal using a sensor or electrodes of, or communicatively coupled to, the IMD.

9. The method of claim 1, wherein:

$16>N>8$; and $M=8$.

10. The method of claim 1, wherein the biological signal comprises one of:

an electrogram (EGM) signal indicative of cardiac electrical activity;

an electrocardiogram (ECG) signal indicative of cardiac electrical activity;

a plethysmography signal indicative of cardiac mechanical activity;

a signal indicative of pressure within a cardiac chamber;

a signal indicative of pressure within a body lumen;

a signal indicative of blood pressure;

a signal indicative of heart sounds;

a signal indicative of body temperature;

a signal indicative of motion; or a cardiogenic impedance signal.

11. The method of claim 1, wherein the IMD comprises one of:

a pacemaker coupled to one or more transvenous leads;

a leadless pacemaker;

an insertable cardiac monitor (ICM); or an implantable cardioverter defibrillator (ICD).

12. An implantable medical device (IMD), comprising:

an N-bit analog-to-digital converter (ADC) that is configured to receive a sensed biological signal, or an amplified and/or filtered version thereof, and output N-bit data values indicative of an amplitude of the biological signal at each of a plurality of points in time, wherein $N > 8$; and a compressor configured to compress the N-bit data values to respective M-bit data values, wherein $M < N$, so that data for the biological signal can be stored as M-bit data slices within memory of the IMD;

wherein for each of the N-bit data values the compressor is configured to select one of a plurality of chords of a compression curve based on which one of a plurality magnitude ranges a magnitude of the N-bit data value output from the ADC is within;

use the selected one of the plurality of chords of the compression curve to produce an M-bit data value, which is a compressed version of the N-bit data value output from the ADC; and store the M-bit data value, or a filtered and/or amplified version thereof, as an M-bit data slice within memory of the IMD, so that the M-bit data value can be expanded to a reproduced N-bit data value after being uploaded to a non-implanted device or system.

13. The IMD of claim 12, further comprising:

memory or registers that store a plurality of look up tables (LUTs), wherein each of the LUTs corresponds to a respective one of the plurality of chords of the compression curve;

wherein the compressor is configured to select one of the plurality of chords of the compression curve by selecting one of the plurality of LUTs based on which one of the plurality magnitude ranges the magnitude of the N-bit data value output from the ADC is within; and wherein the compressor is configured to use the selected one of the plurality of chords of the compression curve to produce the M-bit data value by using the selected one of the plurality of LUTs to produce the M-bit data value.

14. The IMD of claim 13, wherein:

each LUT, of the plurality of LUTs, has a respective different output value for each of a plurality of different sub-ranges of magnitudes, such that the LUT is used to produce a same one of a plurality of different output values for a plurality of different input values that are within a same one of the sub-ranges of magnitudes.

15. The IMD of claim 13, wherein:

in response to receiving instructions from a non-implantable device, the compressor is configured to update one or more of the LUTs stored in the registers or memory to thereby modify how N-bit data values that are output by the ADC are compressed to M-bit data values that are stored in the memory.

16. The IMD of claim 12, wherein:

the compressor comprises a plurality of magnitude comparators and a decoder that receives outputs of the magnitude comparators;

at any given time, each of the magnitude comparators compares a magnitude of a same one of the N-bit data values to a different one of a plurality of reference values that correspond to boundaries of a plurality of magnitude ranges; and the decoder receives the outputs of the magnitude comparators and selects one of the plurality of chords of the compression curve by decoding the outputs of the magnitude comparators.

17. The IMD of claim 12, further comprising:

at least one of a digital filter and a digital amplifier, between the N-bit ADC and the compressor, configured to filter and/or amplify the N-bit data values output from the ADC before the N-bit data values are provided to the compressor.

18. The IMD of claim 12, wherein:

16 >N >8; and

M =8.

19. The IMD of claim 12, wherein the IMD comprises one of:

a pacemaker coupled to one or more transvenous leads;

a leadless pacemaker;

an insertable cardiac monitor (ICM); or an implantable cardioverter defibrillator (ICD).

* * * * *